US012806348B2

(12) United States Patent
Rau et al.

(10) Patent No.: US 12,806,348 B2
(45) Date of Patent: Nov. 24, 2026

(54) FLUID DISPENSING DEVICE

(71) Applicant: Sanofi, Paris (FR)

(72) Inventors: Matthias Rau, Rüsselsheim (DE); Paula Prasch, Rüsselsheim (DE); Beate Franke, Frankfurt am Main (DE); Michael Schabbach, Frankfurt am Main (DE)

(73) Assignee: SANOFI, Paris (FR)

( * ) Notice: Subject to any disclaimer, the term of this patent is extended or adjusted under 35 U.S.C. 154(b) by 1354 days.

(21) Appl. No.: 17/625,194

(22) PCT Filed: Jul. 10, 2020

(86) PCT No.: PCT/EP2020/069500

§ 371 (c)(1),
(2) Date: Jan. 6, 2022

(87) PCT Pub. No.: WO2021/009022

PCT Pub. Date: Jan. 21, 2021

(65) Prior Publication Data

US 2022/0265939 A1 Aug. 25, 2022

(30) Foreign Application Priority Data

Jul. 12, 2019 (EP) .................................... 19305935

(51) Int. Cl.

| | |
|---|---|
| ***A61M 15/00*** | (2006.01) |
| ***A61M 11/00*** | (2006.01) |
| ***A61M 15/08*** | (2006.01) |

(52) U.S. Cl.

CPC ...... *A61M 15/0001* (2014.02); *A61M 11/006* (2014.02); *A61M 15/0025* (2014.02); *A61M 15/009* (2013.01); *A61M 15/08* (2013.01)

(58) Field of Classification Search

CPC ............ A61M 15/0001; A61M 11/006; A61M 15/0025; A61M 15/009; A61M 15/08;

(Continued)

(56) References Cited

U.S. PATENT DOCUMENTS

| | | |
|---|---|---|
| 5,447,150 A | 9/1995 | Bacon |
| 6,415,784 B1 | 7/2002 | Christrup et al. |

(Continued)

FOREIGN PATENT DOCUMENTS

| | | |
|---|---|---|
| CN | 1062091 A | 6/1992 |
| CN | 1320055 A | 10/2001 |

(Continued)

OTHER PUBLICATIONS

International Preliminary Report on Patentability in International Appln. No. PCT/EP2020/069500, dated Jan. 27, 2022, 7 pages.

(Continued)

*Primary Examiner* — Kendra D Carter
*Assistant Examiner* — Arielle Wolff
(74) *Attorney, Agent, or Firm* — Bond, Schoeneck & King, PLLC

(57) ABSTRACT

The disclosure relates to a fluid dispensing device including a housing, a mechanical biasing member, a closure, and a safety arrangement. The housing is configured to accommodate at least a portion of a spray delivery device and an outlet through which the fluid stored in the spray delivery device can be discharged. The mechanical biasing member is reversibly transferable between a pre-loaded state and an unloaded state and configured to store mechanical energy in the pre-loaded state effective to produce a spray discharge of the spray delivery device. The closure is fixable to the housing and movable relative to the housing between a closed position and an open position, wherein when in the open position the container of the spray delivery device is (Continued)

accessible from outside the housing. The movement of the closure is controlled by the safety arrangement.

20 Claims, 21 Drawing Sheets

(58) Field of Classification Search
CPC .......... A61M 15/0026; A61M 15/0016; A61M 15/0081; A61M 2205/8281; A61M 11/007; A61M 2205/276; A61M 15/0091–0098; A61M 11/02
See application file for complete search history.

(56) References Cited

U.S. PATENT DOCUMENTS

| | | | |
|---|---|---|---|
| 9,204,994 B2 | 12/2015 | Greiner-Perth et al. | |
| 2002/0088458 A1 | 7/2002 | Christrup et al. | |
| 2006/0243275 A1 | 11/2006 | Ruckdeschel et al. | |
| 2007/0131717 A1 | 6/2007 | Davies et al. | |
| 2009/0178677 A1 | 7/2009 | Pocock et al. | |
| 2011/0017210 A1 | 1/2011 | Sugianto | |
| 2012/0289907 A1 | 11/2012 | Veasey et al. | |
| 2013/0190703 A1 | 7/2013 | Greiner-Perth et al. | |
| 2014/0109904 A1 | 4/2014 | Kaar et al. | |
| 2014/0123975 A1 | 5/2014 | Sugianto | |
| 2016/0166780 A1 | 6/2016 | Allsop | |
| 2017/0072148 A1* | 3/2017 | Eicher | A61M 15/0065 |
| 2018/0008782 A1 | 1/2018 | Marsh et al. | |

FOREIGN PATENT DOCUMENTS

| | | | |
|---|---|---|---|
| CN | 1901958 | A | 1/2007 |
| CN | 101511416 | A | 8/2009 |
| CN | 102630172 | A | 8/2012 |
| CN | 105407950 | A | 3/2016 |
| CN | 106999655 | A | 8/2017 |
| JP | 2013-539674 | A | 10/2013 |
| JP | 2016-527040 | A | 9/2016 |
| WO | WO 2008/023019 | A2 | 2/2008 |
| WO | WO 2015/018903 | A1 | 2/2015 |
| WO | WO 2017/176693 | | 10/2017 |

OTHER PUBLICATIONS

International Search Report and Written Opinion in International Appln. No. PCT/EP2020/069500, dated Jul. 28, 2020, 8 pages.

* cited by examiner

A-A

A-A

A-A

A-A

A-A

A-A

B-B

B-B

B-B

B-B

B-B

B-B

B-B

FLUID DISPENSING DEVICE

CROSS REFERENCE TO RELATED APPLICATIONS

The present application is the national stage entry of International Patent Application No. PCT/EP2020/069500, filed on Jul. 10, 2020, and claims priority to Application No. EP 19305935.9, filed on Jul. 12, 2019, the disclosures of which are incorporated herein by reference.

TECHNICAL FIELD

The present disclosure relates to the field of fluid dispensing devices and in particular to fluid dispensing devices configured as nasal inhalers. The disclosure further relates to spray devices configured to dispense a fluid or a liquid substance by way of spraying or atomizing.

BACKGROUND

Fluid dispensing devices operable to atomize a liquid substance are as such known. Such devices typically comprise a nozzle or an orifice. Upon application of a force by a user to an actuation lever or a button the fluid is dispensed via the nozzle or orifice. Such devices may be arranged to dispense a single dose or such devices may be equipped with a container providing a reservoir for the fluid thus allowing and supporting the dispensing of several doses.

The efficacy of a dispensing action is dependent upon the manner in which the device is actuated by a user. Dispensing of the fluid is less efficient when an actuation force applied by a user is comparatively low or if the user-induced action is rather slow.

There have been described so called pre-loaded or pre-biased fluid dispensing devices, wherein a force required for a dispensing procedure is provided by a biasing member. Such pre-loaded fluid dispensing devices may be configured to remain in a pre-loaded state for a comparatively long time. With a pre-loaded fluid dispensing device there may be a certain risk of an uncontrolled, premature or inadvertent dispensing of a dose of the fluid. With some fluid dispensing devices a container containing the fluid to be dispensed or delivered is replaceably or interchangeably arranged inside the fluid dispensing device. Replacement of an empty container may require access to the interior of the fluid dispensing device. Especially with fluid dispensing device of pre-loaded or pre-biased type an uncontrolled release of mechanical energy during replacement of a container should be avoided.

SUMMARY

It is desirable to provide an improved fluid dispensing device of pre-loadable type being less susceptible to an uncontrolled, premature or inadvertent dispensing action, in particular during replacement of a container. The fluid dispensing device should provide a rather simple, effective and intuitive approach to prevent an uncontrolled, premature or inadvertent release of mechanical energy during replacement of the container. The intended prevention of uncontrolled, premature or inadvertent dispensing of the fluid should be easily implementable. The respective prevention mechanism should be reliable, robust and durable over the entire lifetime of the fluid dispensing device.

The disclosure relates to a fluid dispensing device. The fluid dispensing device comprises a housing. The housing comprises an orifice and the housing is configured to accommodate at least a portion of a spray delivery device. The spray delivery device comprises a container and an outlet. A fluid, such as a liquid medicament stored in the spray delivery device, in particular stored in the container can be discharged through the outlet, typically by way of spraying.

When appropriately arranged inside the housing or when attached to the housing the outlet of the spray delivery device may cooperate with the orifice of the fluid dispensing device. The fluid dispensing device further comprises a mechanical biasing member reversibly transferrable between a pre-loaded state and an unloaded state. The biasing member is configured to store mechanical energy in the pre-loaded state. The mechanical energy storable in the mechanical biasing member is effective to produce a spray discharge of the spray delivery device. In other words, the biasing member is operable to induce a spray discharge action of the spray delivery device when the spray delivery device is assembled inside or to the housing of the fluid dispensing device.

The fluid dispensing device further comprises a closure fixable to the housing of the fluid dispensing device. The closure is movable relative to the housing between a closed position and an open position. When in the open position at least the container of the spray delivery device or the entirety of the spray delivery device is or are accessible from outside the housing of the fluid dispensing device. When in the closed position the spray delivery device or at least the container of the spray delivery device is and remains inaccessible from outside the housing.

The fluid dispensing device further comprises a safety arrangement. In one example the safety arrangement is configured to prevent a movement of the closure from the closed position towards the open position as long as the mechanical biasing member is in the pre-loaded state. Alternatively, the movement of the closure from the closed position towards the open position is prevented by the safety arrangement as long as the mechanical biasing member is transferable from the pre-loaded state into the unloaded state. Here, and as long as the biasing member is or remains in the pre-loaded state the safety arrangement is configured to block or to prevent a movement of the closure form the closed position towards and/or into the open position.

With a further example the safety arrangement is configured to prevent a release of mechanical energy of the mechanical biasing member as long as the closure is not in the closed position. Alternatively, and according to a third example the safety arrangement is configured to release at least a portion or the entirety of the mechanical energy of the pre-loaded mechanical biasing member during and/or through a movement of the closure from the closed position towards and/or into the open position.

The safety arrangement is configured and operable to prevent an uncontrolled release of the mechanical energy stored in the mechanical biasing member during and/or for replacement of the container or of the entirety of the spray delivery device. In this way, an uncontrolled discharge of the spray delivery device can be prevented in such configurations in which the fluid dispensing device is subject to a reconfiguration, in particular when an empty container or when the entirety of the spray delivery device assembled inside the fluid dispensing device is subject to a replacement.

The safety arrangement is further operable and configured to maintain an assembly, hence an assembly configuration of the fluid dispensing device, which may otherwise become distorted when the mechanical energy of the mechanical biasing member would be released in an uncontrolled way, e.g. when the closure is in the open position or when the closure is transferred into the open position.

With those examples, wherein the safety arrangement is configured to prevent a movement of the closure from the closed position towards and into the open position as long as the mechanical biasing member is in the pre-loaded state, the closure is effectively locked and cannot be opened or transferred into the open position. Transfer of the closure from the closed position towards and/or into the open position requires a transfer of the mechanical biasing member from the pre-loaded state into the unloaded state as a prerequisite. When arriving or approaching the unloaded state the safety arrangement may release a respective lock. The safety arrangement then allows and/or supports transferring of the closure from the closed position towards and into the open position.

With other examples, wherein the safety arrangement is configured to prevent a release of mechanical energy of the mechanical biasing member as long as the closure is not in the closed position the safety arrangement is operably engaged with the mechanical biasing member either directly or indirectly. Here, the safety arrangement is configured to determine whether the closure is in the closed position. As long as the closure is in the open position and/or as long as the closure is not in the closed position the safety arrangement is configured and operable to keep the mechanical biasing member in the pre-loaded state. Here, the safety arrangement prevents an uncontrolled release of the mechanical energy of the mechanical biasing member. Release of mechanical energy from the mechanical biasing member is only possible when the closure is in the closed position. In all other positions of the closure the release of mechanical energy from the mechanical biasing member is blocked and/or prevented.

With further examples and when the safety arrangement is configured to release at least a portion or the entirety of the mechanical energy of the pre-loaded mechanical biasing member during and/or through a movement of the closure from the closed position towards the open position the safety arrangement serves to dissipate at least a portion of the mechanical energy of the mechanical biasing member in a controlled way. With such examples transferring of the closure from the closed position towards and into the open position is possible even with the mechanical biasing member being pre-loaded.

But here and during the movement of the closure from the closed position towards the open position the mechanical energy of the pre-loaded mechanical biasing member is released in such a way, that when the closure reaches the open position the mechanical energy of the pre-loaded mechanical biasing member has been reduced to such a degree that a remaining or residual mechanical energy stored in the mechanical biasing member is ineffective to produce a spray discharge of the spray delivery device and/or that the remaining mechanical energy is ineffective to distort or to rearrange the assembly of exchangeable components inside the housing of the fluid dispensing device. Here and during the movement of the closure from the closed position towards the open position the closure is and remains fixed or attached to the housing until it reaches the open position.

According to a further example the safety arrangement comprises a carrier. The carrier is mechanically engageable with the spray delivery device or with a moveable part of the spray delivery device. For instance, the carrier is connectable and/or fixable to the spray delivery device or to a moveable part thereof. The carrier and the spray delivery device or the moveable part of the spray delivery device are for instance frictionally engageable or they are in fact frictionally engaged. With further exampled they are engageable via a positive fit or they are positively engaged.

The carrier is mechanically engaged with the mechanical biasing member. The carrier is moveable inside the housing from an unbiased position against a force effect of the mechanical biasing member towards and into a biased position. Hence, the carrier is transferrable through the action of the mechanical biasing member from the biased position into the unbiased position. The carrier is effective to transfer a force effect of the mechanical biasing member to the spray delivery device or to the moveable part of the spray delivery device.

In particular, the carrier provides a mount and/or a receptacle for the spray delivery device inside the housing of the fluid dispensing device. In this way the spray delivery device and/or a moveable part thereof can be detachably arranged to the carrier and hence can be detachably arranged inside the housing of the fluid dispensing device.

According to a further example and when in the biased position the carrier is engaged with the closure. When in the biased position the carrier prevents a movement of the closure from the closed position towards the open position. Here, the carrier serves as a closure lock effective to keep the closure in the closed position as long as the carrier is in the biased position. The closure and hence the closure lock is transferrable from a locked state into an unlocked state by moving the carrier under the action of the mechanical biasing member towards and/or into the unbiased position. In this way it is somehow guaranteed, that the closure is only moveable from the closed position towards the open position when the carrier is in the unbiased position and when the mechanical biasing member is in the unloaded state. When opening the housing of the fluid dispensing device by moving the closure from the closed position towards and into the open position the mechanical biasing member is in the unloaded state.

According to a further example the closure is connectable to the housing via threaded joint or bayonet joint. For transferring the closure from the closed position into the open position the closure rotates relative to the housing with regard to a longitudinal axis as an axis of rotation. For transferring the closure from the closed position into the open position the closure is subject to a helical motion with regards to the longitudinal axis. According to a lead of the threaded engagement between the closure and the housing and/or according to a lead of the bayonet joint the closure is subject to a combined rotational and longitudinal motion with regard to the longitudinal axis. The threaded engagement may be of self-locking type. Hence, the lead of the mutually corresponding threaded or helically slotted portions of the housing and the closure are selected such that a force effect emanating from the mechanical biasing member is insufficient to initiate a release of the threaded connection between the housing and the closure.

With this example the closure is detachably connectable to the housing. When arriving in the open position the closure may be disconnected from the housing. It may be hence taken away from the housing.

With other examples the closure is permanently connected to the housing. It may be pivotally connected to the housing through and by a pivot joint.

According to a further example the carrier is rotationally locked to the housing and the carrier is slidably displaceable relative to the housing along the longitudinal axis. Hence, the carrier is in a first longitudinal position when the carrier is in the biased position. The carrier is in a second longitudinal position when in the unbiased position. Transferring the carrier from the biased position towards and into the unbiased position comes along with a longitudinal displacement of the carrier from the first longitudinal position towards and into the second longitudinal position. In the first longitudinal position the carrier may be operably engaged and locked to the closure. When in the second longitudinal position the carrier may be operably disengaged and hence unlocked from the closure.

Engagement and disengagement of the carrier with and from the closure comes along with or is accompanied by a displacement of the carrier relative to the housing along the longitudinal direction.

Moreover, when the carrier is slidably displaceable relative to the housing along the longitudinal axis it may be rotationally locked to the housing. In this way and in particular when the carrier is in the biased position and hence in the first longitudinal position it may be rotationally locked to the closure. This is of particular benefit when the closure is connected to the housing by a threaded joint or by a bayonet joint. Here, and as long as the carrier is in the biased position or in the first longitudinal position, a rotational movement of the closure relative to the housing is blocked through the rotational lock with the carrier while the carrier itself is rotationally locked to the housing.

A displacement of the carrier from the first longitudinal position towards and/or into the second longitudinal position provides a disengagement of the carrier from the closure. At least when arriving in the second longitudinal and hence in the unbiased position the closure is free to rotate relative to the housing. Accordingly, the bayonet joint or the threaded joint between the housing and the closure can be released or opened.

Hence, and according to a further example, the closure is rotationally engaged or rotationally locked to the carrier when the carrier is in the biased position. The closure is rotationally released from the carrier when the carrier is in or when the carrier approaches the unbiased position.

According to a further example the fluid dispensing device comprises a releasable interlock configured to retain the biasing member in the pre-loaded state. The fluid dispensing device further comprises a manually actuatable trigger. The trigger is operationally engaged with the interlock and is configured to release the interlock when the trigger is actuated.

A trigger-actuation induced release of the interlock releases the biasing member from the pre-loaded state and allows the biasing member to transfer into the unloaded state, thus releasing mechanical energy to induce or to effectuate a spray discharge of the spray delivery device.

According to a further example, the safety arrangement is configured to block an actuation of the trigger or to block a release of the interlock as long as the carrier is in the biased position. In this way the safety arrangement is configured to prevent a release of mechanical energy of the mechanical biasing member as long as the carrier is in the biased position and/or as long as the mechanical biasing member is in the pre-loaded state. Here, the safety arrangement is configured to prevent an uncontrolled release of mechanical energy as long as the carrier is in the biased position.

With further examples the safety arrangement is configured to block an actuation of the trigger or to block a release of the interlock as long as the closure is in the open position and/or as long as the closure is not in the closed position. Here, the safety mechanism may be implemented or configured to allow actuation of the trigger and/or to allow and to support release of the interlock only when the closure is in the closed position. In this way, an uncontrolled release of mechanical energy from the mechanical biasing member during an exchange operation of the spray delivery device or of its container can be effectively prevented.

According to a further example the closure is engaged with at least one of the interlock and the trigger. The closure is transferrable or moveable from the closed position into the open position only when the interlock is released or when the trigger is actuated. In this way opening of the closure requires a preceding release of the mechanical biasing member. Hence, opening of the closure or transferring of the closure into the open position requires that the mechanical biasing member is transferred into the unloaded state either by transferring the interlock into the unlocked state and/or by transferring the trigger into the actuated position.

In both configurations, i.e. when the trigger is in the actuator position or when the interlock is in the unlocked state, the mechanical energy of the mechanical biasing member is effectively released and the mechanical biasing member assumes or approaches the unloaded state.

According to a further example the trigger is displaceable relative to the housing from an idle position into the actuated position. In the idle position the trigger is depressible or actuatable for release of the interlock. Hence, in the idle position the trigger is ready to become actuated.

With some examples the trigger is actuatable along a transverse direction with regard to the longitudinal direction of the housing. When in the idle position the trigger is engaged with the closure and when in the actuated position the closure is disengaged from the trigger. When the trigger is engaged with the closure the closure is effectively locked to the housing. By actuating the trigger and hence by moving the trigger along the transverse direction a closure lock between the closure and the housing can be released. In this way transferring of the closure from the closed position towards and/or into the open position requires actuation, e.g. depression of the trigger.

According to a further example at least one of the trigger and the interlock is operably engaged with the closure. The at least one of the trigger and the interlock is transferrable into the unlocked state or actuated state only when the closure is in the closed position.

Here, the safety arrangement provides a mechanical coupling between the closure and at least one of the interlock and the trigger. A release of the interlock and/or actuation of the trigger requires that the closure is in the closed position. Otherwise, unlocking of the interlock and/or actuating of the trigger is effectively blocked by the safety arrangement as long as the closure is in the open position and/or when the closure is not in the closed position. In this way it is guaranteed, that release of the mechanical energy of the mechanical biasing member can only take place when the closure is in the closed position. An inadvertent release of mechanical energy while the closure is open can be effectively prevented.

According to a further example the fluid dispensing device comprises a protective cap. The protective cap is configured to accommodate the outlet of the spray delivery device. The protective cap is further configured for fitting to the housing at least in a closing position relative to the housing. In the closing position the protective cap covers the orifice of the housing. The protective cap is displaceable between a closing position and an open position. In the open position or before reaching the open position the protective cap may no longer cover or obstruct the orifice.

With some examples the protective cap is mechanically engaged with at least one of the interlock and the trigger when in the closing position. Typically and when in the closing position and when covering the orifice the protective cap effectively blocks and hinders a dispensing action of the fluid dispensing device, which dispensing action may be initiated and/or effectuated by the mechanical biasing member.

With some examples and as long as the protective cap is in the closing position actuation of the trigger to release the interlock and/or to release the biasing member is effectively blocked or hindered. Moreover, and as long as the protective cap is in the closing position, a manipulation or actuation of the interlock can be effectively blocked and hindered. Here, the interlock remains in the locked state, in which the mechanical biasing member is retained and/or fixed in the pre-loaded state.

With some examples and as long as the protective cap is in the closing position a dispensing operation of the fluid dispensing device is effectively blocked. Here, an uncontrolled, premature or inadvertent dispensing of the fluid can be effectively prevented as long as the protective cap is in the closing position.

With some examples the protective cap is at least one of detachably connectable to the housing, pivotally connected to the housing and slidably connected to the housing. Transferring of the protective cap from the closing position into the open position includes one of detaching, pivoting or sliding the protective cap relative to the housing in order to uncover and to reveal the orifice of the housing and/or the outlet of the spray discharge device.

According to a further example the protective cap is mechanically engaged with at least one of the interlock and the trigger when in the closing position. Hence, when in the closing position the protective cap is operable or configured to block actuation of the trigger. For this, the protective cap may comprise a blocking portion to engage or to cooperate with the trigger. As long as the protective cap is in the closing position the blocking portion thereof hinders activation, e.g. a depression of the trigger relative to the housing.

With other examples the protective cap covers the trigger when and as long as it is in the closing position. Here, the trigger is arranged close to a portion of the housing that is covered by the protective cap when in the closing position. When and as long as the protective cap is in the closing position at least a portion thereof covers and/or obstructs the trigger. In this way and as long as the protective cap is in the closing position the trigger is and remains inaccessible for the user. The trigger simply cannot be actuated for dispensing or delivery of a dose of the fluid. Accordingly and with these examples when and as long as the protective cap is in the closing position it is operable to block the trigger, to cover the trigger and/or to block a release of the interlock.

Hence, the protective cap or a portion thereof may be operably engageable not only with the trigger but also with the interlock when the protective cap is in the closing position. The protective cap may be operably engageable exclusively with the interlock when in the closing position. It may be operably engaged with both, the interlock as well as with the trigger when the protective cap is in the closing position.

According to a further example the fluid dispensing device comprises a closure lock engaged with the housing and engaged with the closure. The closure lock is transferable between a locked state, in which the closure is locked to the housing and an unlocked state, in which the closure is moveable relative to the housing. Transfer of the closure from the closed state towards and into the open state is only possible when the closure lock is in the unlocked state. As long as the closure lock is in the locked state the closure is effectively locked to the housing and cannot be moved from the closed position towards and/or into the open position.

According to another example the closure lock comprises a latch on one of the housing and the closure. The closure lock further comprises a latch keeper on the other one of the housing and the closure. The closure lock is in the locked state when the latch is engaged with the latch keeper. The closure lock is in the unlocked state when the latch and the latch keeper are disengaged. The latch may be mechanically biased, e.g. by a lock spring effective to bring the latch in engagement with the latch keeper as soon as the latch is aligned to the latch keeper. In this way a self-actuated closure lock can be implemented.

As long as the closure lock is in a locked state it effectively prevents a movement, e.g. a rotation of the closure relative to the housing. Hence, the closure lock effectively prevents opening of the housing as long as it is in the locked state.

According to a further example the closure lock is operably engaged with at least one of the interlock, the trigger and the protective cap. The closure lock is transferable from the locked state towards or into the unlocked state by the at least one of the interlock, the trigger and the protective cap. Transfer of the closure lock from the locked state towards or into the unlocked state may require that the interlock is unlocked, thus leading to a release of the mechanical energy of the mechanical biasing member. Similarly, transferring of the closure lock into the unlocked state may require actuation of the trigger also leading to a release of the mechanical energy of the mechanical biasing member.

With further examples transferring of the closure lock from the locked state towards and into the unlocked state may require that the protective cap is in the closing position. Typically and when in the closing position the protective cap keeps the interlock and/or the trigger in the locked state or in an idle position, respectively. In this way and when mechanically engaged with the protective cap the closure lock is only and exclusively transferrable from the locked state into the unlocked state when the protective cap is in the closing position, in which actuation of the trigger and/or unlocking of the interlock is effectively blocked by the protective cap.

The requirements of unlocking the closure lock only when the protective cap is in the closing position has the further benefit, that the orifice of the housing is effectively covered and closed by the protective cap. So even in situations, in which the mechanical energy of the mechanical biasing member can be inadvertently released during a replacement of the container or of the spray delivery device the fluid cannot dissipate in an uncontrolled way into the vicinity of the fluid dispensing device.

According to another example the fluid dispensing device comprises a closure lock rod slidably disposed in the housing. The closure lock rod comprises a first end and a second end opposite the first end. The first end is configured to engage with one of the interlock, the trigger and the protective cap. The second end of the closure lock rod is configured to engage with the closure lock.

In this way a motion or configuration of at least one of the interlock, the trigger and the protective cap can be transferred to the closure lock by and/or through the closure lock rod. With some examples the closure lock and the closure may be located at a bottom portion of the housing. The interlock, the trigger and/or the protective cap may be located at a top portion, hence at an opposite end of the housing compared to the closure. In this way, the closure lock rod provides a mechanical coupling between at least one of the interlock, the trigger and the protective cap with the closure lock.

According to another example the mechanical biasing member further comprises a first end and a second end. The first end is operably engaged with the spray delivery device. The second end is engaged with the closure or with the housing of the fluid dispensing device.

By arranging the mechanical biasing member between the spray delivery device and the closure provides the benefit, that the mechanical biasing member may release at least a portion of its mechanical energy during a movement of the closure from the closed position towards and into the open position. Transferring of the closure from the closed position into the open position may require a displacement of the closure along a path comprising at least a certain extension along a longitudinal extension of the housing. When the mechanical biasing member also extends along the longitudinal direction, movement of the closure along the respective path from the closed position towards the open position comes along with a respective unloading of the mechanical biasing member. The displacement path of the closure between the closed position and the open position may be that large that the mechanical energy of the mechanical biasing member is effectively released or unloaded when the closure arrives in the open position. During a displacement along the displacement path and before reaching the open position the closure remains fixed to the housing.

According to a further example a movement of the closure from the closed position towards the open position includes a movement of the closure along an elongation of the mechanical biasing member extending from the first end to the second end such that the distance between the first end to the second end increases. Here, the mechanical biasing member may be implemented as a compression spring that can be compressed along a longitudinal direction against a restoring force of the compression spring. Hence, the mechanical biasing member is configured to maximize the longitudinal distance between the first end and the second end. Mechanical energy is stored by the mechanical biasing member by bringing together the first end and the second end and/or by moving one of the first end and the second end towards the other one of the first end and the second end.

With further examples the closure forms a bottom end of the housing. Here, the closure may be threadedly engaged with the housing or the closure may be fixed to the housing by way of a bayonet joint. With both, a threaded engagement or threaded joint and a bayonet joint between the closure and the housing, transferring of the closure from the closed position towards and into the open position comes along with a respective displacement of the closure along the longitudinal direction of the housing. Such a movement is accompanied by an increase of the distance between the first end of the mechanical biasing member relative to the second end of the mechanical biasing member. Accordingly and as the closure is moved from the closed position towards the open position the mechanical biasing member is subject to unloading or dissipation of mechanical energy.

According to another example the closure comprises a compartment accommodating at least a portion of the container. By transferring the closure from the closed position into the open position the compartment of the closure is subject to a movement relative to the container located inside the housing. As the compartment reaches the open position at least a portion of the container that is located inside the compartment when the closure is in the closed position is now accessible from outside the housing. Here, a user may grip the container and may dismount the container from the housing. The container may be replaced by a new container and the closure may be reattached or may return into the closed position.

According to a further example the compartment of the closure accommodates the mechanical biasing member and a pressure piece. Here, the pressure piece is engaged with or is connectable to the first end of the mechanical biasing member. The pressure piece is further engageable with the container of the spray delivery device. The pressure piece may be displaceable inside the compartment against the action of the mechanical biasing member. With some examples the pressure piece is slidably arranged inside the compartment. The pressure piece may be displaceable against the action of the mechanical biasing member when getting into engagement with the spray delivery device, in particular with a container of the spray delivery device.

In this way and upon transferring of the closure from the open position towards and into the closed position the pressure piece may get into abutment, e.g. with a bottom portion of the container of the spray delivery device. As the closure is subject to a closing motion relative to the housing the abutment between the pressure piece and the container may lead to a displacement of the pressure piece relative to the compartment and relative to the closure against the action of the mechanical biasing member.

According to another example the compartment comprises a partition wall with a through opening. At least a portion of the container extends through the through opening into the compartment when the closure is in the closed position. The through opening is sized to receive the container therethrough. The through opening may comprise an inner cross-section that corresponds to an outer cross-section of the container. In this way, the container is configured to enter and to extend through the through opening of the partition wall into the compartment.

With further examples an inner cross-section of the through opening of the partition wall is smaller than a cross-section of the pressure piece. In this way, the pressure piece and the mechanical biasing member are permanently located inside the compartment of the closure.

They cannot escape from the compartment through the through opening, even if mechanical energy can be dissipated in an uncontrolled way from the mechanical biasing member.

Typically, the pressure piece is located between a first end of the mechanical biasing member and the partition wall of the compartment. The partition wall of the compartment may be located opposite a bottom portion of the compartment. The bottom portion of the compartment may coincide with a bottom portion of the closure.

The closure itself may form a bottom portion of the housing.

With some examples the through opening of the partition wall may be further sized to receive the carrier therethrough. In this way, the through opening may fulfill a double or twofold function. On the one hand it prevents a disassembly of the mechanical biasing member when the closure is in the open position. On the other hand it provides a longitudinal guidance for a sliding displacement of the carrier relative to the housing and/or relative to the closure.

According to another independent aspect transferring of the mechanical biasing member between the pre-loaded state and the unloaded state includes a movement of at least a portion of the mechanical biasing member along a longitudinal direction. Here, at least one of the closure and the container is moveable along a replacement direction for replacement of the container. The replacement direction extends transverse to the longitudinal direction. In this way and since the mechanical force emanating from the mechanical biasing member extends nonparallel, e.g. even perpendicular to a replacement direction along which the container is moveable relative to the housing for replacing the container, an inadvertent release of mechanical energy can be effectively prevented and/or an inadvertent release of mechanical energy has no substantial effect on the spray delivery device. With such examples the safety arrangement is simply provided or constituted by the nonparallel alignment of the replacement direction and the longitudinal direction.

In this way an inadvertent delivery or expelling of a dose of the fluid from the spray delivery device during a replacement of the container and/or when the closure is in an open position can be effectively prevented.

According to another example the spray delivery device or a portion thereof is arranged inside the housing. The outlet of the spray delivery device coincides with the orifice or is arranged in an alignment with the orifice. Typically, the spray delivery device comprises a first part, e.g. a moveable part and a second part, e.g. a container. One of the first part and the second part is engaged with or is attached to the housing of the fluid dispensing device whereas the other one of the first part and the second part is attached to or is engaged with the mechanical biasing member.

With some examples the second part of the device, e.g. the container is stationary fixed inside the housing. Here, the second part, e.g. the moveable part is operably engaged with at least one of the biasing member and the mechanical coupler. With another example it is the first part, e.g. the moveable part that is fixed inside the housing of the fluid dispensing device. Then, at least one of the biasing member and the mechanical coupler is engaged with, attached to or fixed to the second part of the spray delivery device, e.g. fixed to the container. With any configuration the biasing member is operable to provide a dispensing force which is effective to induce a displacement or movement of the first part relative to the second part of the spray delivery device.

According to an example, the spray delivery device comprises a movable part and a container, wherein the movable part. the container provides a reservoir for the fluid. The movable part is displaceable relative to the container between a preload position and a discharge position. the spray delivery device further comprises the outlet as described above. Moving of the movable part relative to the container is effective to discharge the spray jet from the outlet. With some examples the outlet is integrally formed with the movable part. The outlet will then be movable relative to the container. With other example, the outlet is stationary relative to the container. Then, the movable part is movable relative to the both, the outlet and the container.

Typically, the container of the spray delivery device is at least partially filled with a drug or medicament. The container may comprise a prefilled container being prefilled with the respective drug or medicament. The container and hence the entire spray delivery device may be preassembled inside the housing and hence inside the fluid dispensing device.

According to a further example at least one of the outlet and the container of the spray delivery device is fixed inside the housing of the fluid dispensing device. Here, the moveable part of the spray delivery device is mechanically engaged with or is connected to the mechanical biasing member. In this way, a biasing member-induced displacement of the moveable part relative to the container of the spray delivery device can be provided.

With another example the outlet of the spray delivery device is fixed to the moveable part of the spray delivery device. Then, the container of the spray delivery device is mechanically engaged with or is connected to the mechanical biasing member. While the outlet and the moveable part of the spray delivery device are both fixed relative to each other as well as to the housing of the fluid dispensing device it is the container of the spray delivery device that is mechanically engaged, hence fixed or connected to the mechanical biasing member. In this way the biasing member may either directly or indirectly, i.e. via the mechanical coupler, induce a displacement, e.g. a longitudinal motion of the container relative to the moveable part of the spray delivery device. In this way, a dose of the fluid can be dispensed.

The outlet and the moveable part may be mutually connected or they may be integrally formed. Hence, the outlet may be incorporated or integrated into the moveable part. It is then of particular benefit, that the outlet and/or the moveable part of the spray delivery device is connected to the housing of the fluid dispensing device, typically the outlet of the spray delivery device directly communicates with the nozzle of the fluid dispensing device in a fluid transferring way.

With some further examples the spray delivery device comprises a base. Here, the outlet of the spray delivery device is moveable relative to the base for discharging a dose of the fluid through the outlet. With some examples one of the base and the outlet is a moveable part of the spray delivery device that is moveable by the mechanical biasing member relative to the other one of the base and the outlet.

Typically, one of the base and the outlet is connected to the housing and the other one of the base and the outlet is connected to or is mechanically engaged with the mechanical biasing member.

With some examples and according to another independent aspect the fluid dispensing device comprises a housing as described above and comprises a mechanical biasing member as described above. The fluid dispensing device further comprises a closure fixable to the housing and moveable relative to the housing between a closed position and an open position. When in the open position the container of the spray delivery device is accessible from outside the housing. Instead of a safety arrangement at least the container of the spray delivery device is arranged outside or remote of the flux of force emanating from the mechanical biasing member.

Here, the container of the spray delivery device may be releasably attachable to the base of the spray delivery device and the base of the spray delivery device may be fixedly or detachably connected to the housing of the fluid dispensing device. With such examples the mechanical biasing member is only active between the base and the outlet of the spray delivery device. The base may be non-moveably attachable or non-moveably fixable to the housing and the outlet of the spray delivery device may be displaced relative to the base under the action of the mechanical biasing member. With other examples the base of the spray delivery device is displaceable relative to the outlet of the spray delivery device under the action of the mechanical biasing member, but here the base is e.g. slidable between a first and a second stop position inside the housing such that even with an open closure the base of the spray delivery device is and remains fixed or assembled inside the housing of the fluid dispensing device.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof. Moreover, the examples as illustrated herein can be combined. Features of the device disclosed in connection with only one example may equally apply to further examples or embodiments as disclosed herein.

BRIEF DESCRIPTION OF THE FIGURES

In the following, various benefits, effects and features of numerous examples of the fluid dispensing device are described in more detail by making reference to the drawings, in which.

DETAILED DESCRIPTION

Figure 1:
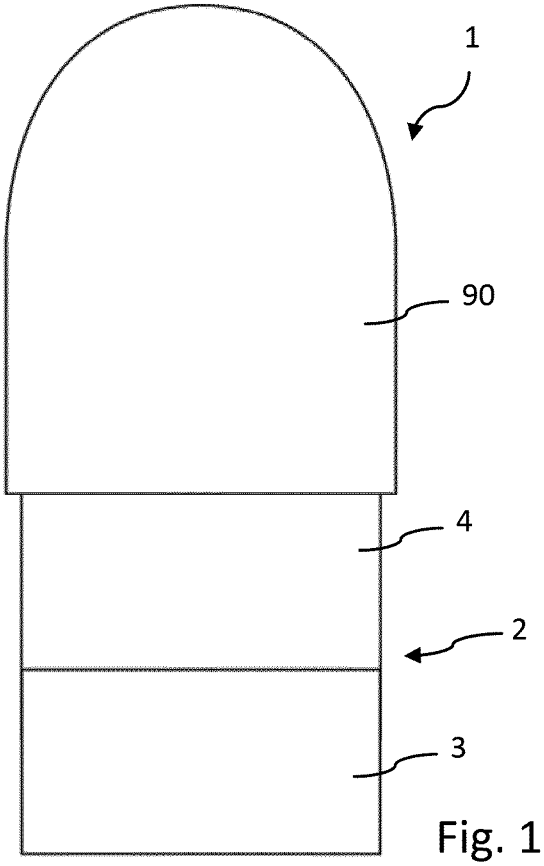
FIG. 1 is a schematic side view of an example of a fluid dispensing device.
Figure 2:
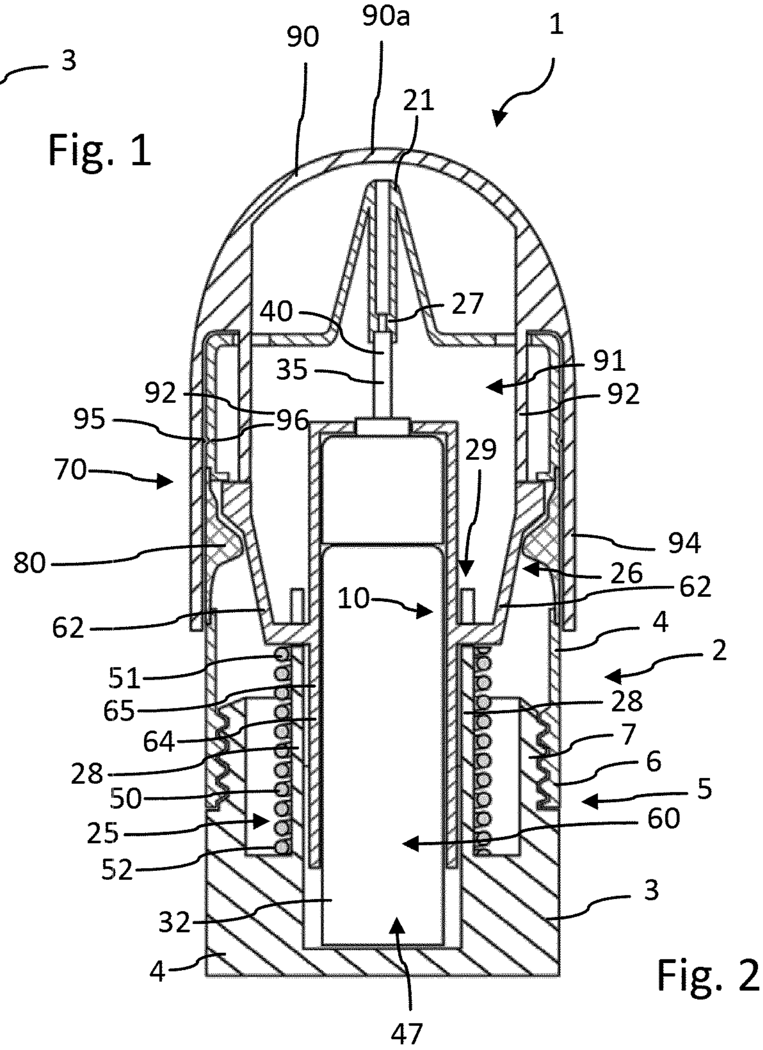
FIG. 2 is a cross-section through the device according to FIG. 1.

FIG. 1 illustrates a side view of one example of a fluid dispensing device 1 configured as a nasal inhaler. The fluid dispensing device 1 comprises a housing 2. The housing 2 is configured to accommodate a spray delivery device 30 as illustrated in the cross-section of FIG. 2. The housing 2 comprises an orifice 21 at an upper end or distal end configured to dispense an amount of a fluid provided in or provided by the spray delivery device 30. The fluid dispensing device 1 further comprises a protective cap 90. In the closing position as illustrated in FIG. 2 the protective cap 90 covers the entire upper section or upper end of the housing 2 and particularly covers the orifice 21.

It is generally sufficient, that only a portion of the protective cap 90, i.e. a cap portion 90*a* covers at least a part of the orifice 21. In the closing position as illustrated in FIGS. 1 and 2 an interior space 91 of the cup-shaped protective cap 90, e.g. comprising a hollow interior effectively covers the orifice 21.

Inside the housing 2 there is provided an accommodation space 26 configured to receive and to hold at least a part of the spray delivery device 30. The spray delivery device 30 may be preassembled inside the housing 2 and is replaceably assembled and arranged inside the housing 2. The spray delivery device 30 as illustrated in FIG. 2 is representative of either a first or second type of spray delivery device as will be explained in greater detail with respect to FIGS. 48-53.

Figure 48:
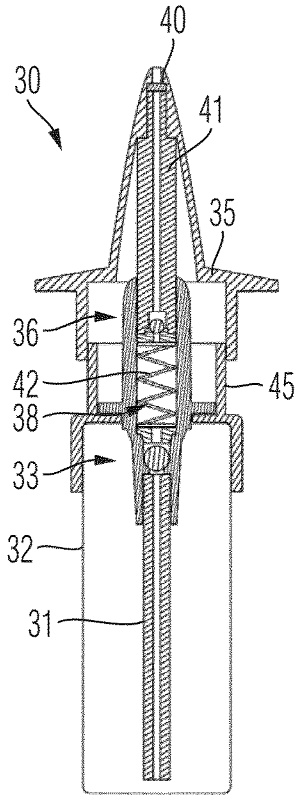
FIG. 48 is illustrative of a first type of a spray delivery device in an initial configuration.
Figure 49:
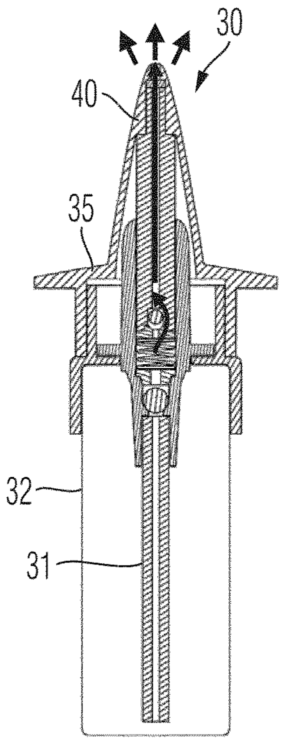
FIG. 49 shows the spray delivery device of FIG. 48 during a dispensing operation and FIG. 50 is illustrative of the device of FIGS. 48 and 49 during a recovery.
Figure 50:
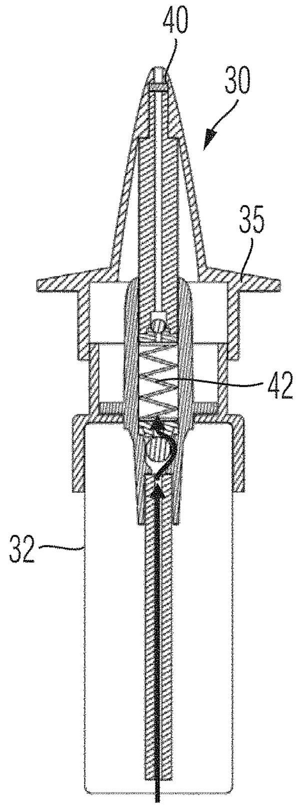
Figure 51:
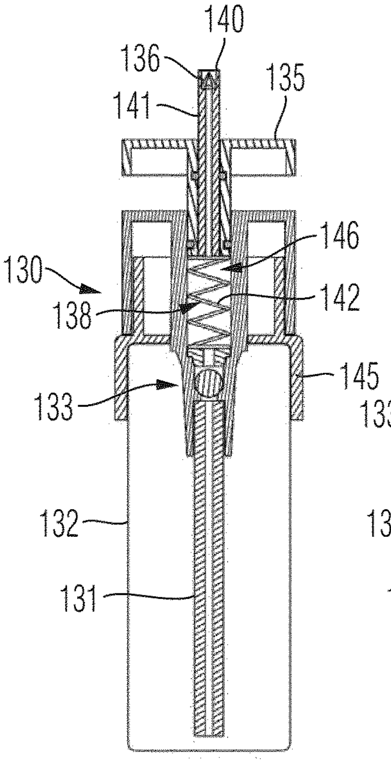
FIG. 51 shows a second type of a spray delivery device in an initial configuration.
Figure 52:
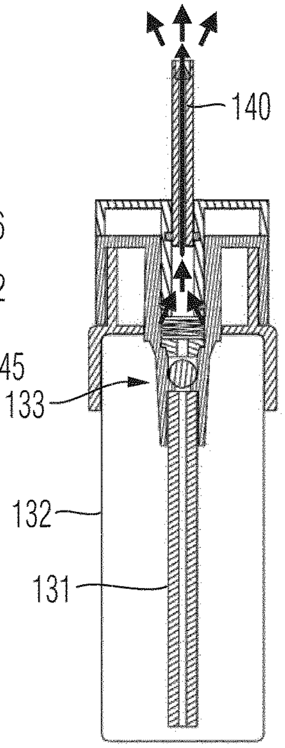
FIG. 52 shows the spray delivery device of FIG. 51 during a dispensing operation and FIG. 53 shows the spray delivery device of the second type during a recovery.
Figure 53:
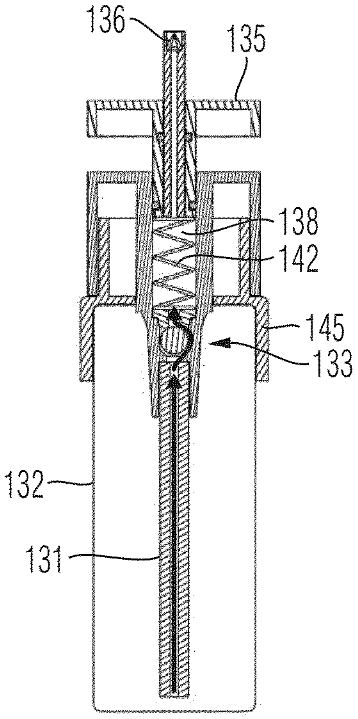

In FIGS. 48-50 a first type of a spray delivery device 30 is illustrated. In FIGS. 51-53 a second type of a spray delivery device 130 is illustrated. The spray delivery device 30 comprises a container 32 configured to receive and to hold an amount of a liquid substance, hence a fluid intended for dispensing. The spray delivery device 30 further comprises a moveable part 35 that is moveable relative to the container 32. The spray delivery device 30 further comprises an outlet 40. With the first type of spray delivery device 30 as illustrated in FIGS. 48-50 the moveable part 35 and the outlet 40 are mutually connected and fixed. They may even be integrally formed. Here, the outlet 40 can be regarded as a first part of the spray delivery device 30 and the container 32 can be regarded as a second part of the spray delivery device 30.

Optionally, the spray delivery device 30 further comprises a base 45 that is attached to an upper or outlet end of the container 32. The container 32 is open towards the base 45. The base 45 further comprises a hollow chamber 38. A tube 31 is connected to the base 45. The tube 31 may be implemented as a suction tube and extends into the interior of the container 32. The tube 31 is in flow connection with the hollow chamber 38. Inside or outside the chamber 38 there is provided a spring 42. The spring 42 is configured to bias the moveable part 35 away from the container 32, hence in an upright or upwards direction as illustrated in FIG. 48. The base 45 is further equipped with an inlet valve 33. The inlet valve 33 is arranged between the tube 31 and the chamber 38. The base 45 further comprises an outlet valve 36 that is arranged between the chamber 38 and the outlet 40. As illustrated in FIG. 48, the upper or free end of the moveable part 35 is in flow communication with the chamber 38 through an elongated and rigid hollow shaft 41.

In an initial configuration as illustrated in FIG. 48 the chamber 38 is filled with the liquid substance withdrawn from the interior of the container 32. If a user now applies a pressure onto the moveable part 35 effective to move the moveable part 35 towards the container 32 the shaft 41 enters the chamber 38 displaces the fluid located inside the chamber 38. The fluid can only escape via the hollow shaft 41 towards the outlet 40. During the displacement of the moveable part 35 relative to the container 32 the inlet valve 33 is closed thus impeding that the fluid located inside the chamber 38 could re-enter the container 32.

After release of the moveable part 35 the spring 42 is operable to drive the moveable part 35 and the container 32 apart from each other. In the configuration as illustrated in FIG. 50, the spring 42 is operable to displace the moveable part 35 away from the container 32. This leads to an under pressure in the chamber 38 and thus to a suction-based withdrawal of a further dose of the fluid from the container 32 through the tube 31 and into the chamber 38. Then, the chamber 38 is filled again and the spray delivery device 30 of the first type is ready for a subsequent dispensing procedure that may be initiated by repeatedly depressing or displacing the moveable part 35 relative to the container 32.

The spray delivery device 130 of the second type as illustrated in FIGS. 51-53 works in accordance to a similar principle. Similar or like components compared to the spray delivery device 30 as illustrated in FIGS. 48-50 are provided with the same reference numbers increased by 100. Also here, the spray delivery device 130 comprises a container 132, a moveable part 135 and an outlet 140. The spray delivery device 130 further comprises a base 145 attached to an outlet end of the container 132. A tube 131 connected to a chamber 138 of the spray delivery device 130 is arranged inside the interior of the container 132. Between the chamber 138 and the tube 132 there is provided an inlet valve 133. An outlet valve 136 is provided at the free end of the outlet 140. The outlet valve 136 may be implemented as a duckbill valve.

The working principle of the second type of the spray delivery device 130 is comparable to the working principle of the first type of spray delivery device 30. In an initial configuration as illustrated in FIG. 51 the chamber 138 is filled with the fluid. But here and contrary to the first type of spray delivery device 30 the outlet 140 is fixed to the base 145. Rather, the moveable part 135 is displaceable relative to the container 132 as well as relative to the outlet 140 against the action of the spring 142. As indicated in FIGS. 51-53, the base 145 provides an elongated hollow shaft in which the moveable part 135 is allowed to slide under and against the action of the spring 142.

As the moveable part 135 is depressed the moveable part 135 at least partially enters the chamber 138 and displaces the liquid contained therein. During this motion as illustrated in FIG. 52 the inlet valve 133 is closed. So the liquid can only be expelled through the hollow and rigid shaft 141 towards the outlet 140. The outlet valve 136 allows and supports dispensing and/or atomization of the fluid.

Thereafter and upon release of the moveable part 135 the relaxing spring 142 is effective to displace the moveable part 135 away from the container 132. Since the outlet valve 136 is effectively closed the spring-induced movement of the moveable part 135 leads to the build-up of a negative pressure inside the chamber 138. The negative pressure serves to open the inlet valve 133 and to withdraw a further amount of the liquid from the interior of the container 132 into the chamber 138. Here, the movable part 135 can be regarded as a first part of the spray delivery device 130 and at least one of the outlet 140 and the container 132 can be regarded as a second part of the spray delivery device.

It can be noted, that both of the first and second types of spray delivery devices 30, 130 are equally applicable to the numerous examples of fluid dispensing devices 10, 100 as described herein.

For a dispensing operation it is only required that the moveable part 35, 135 is subject to a displacement relative to the container 32, 132.

Returning to the example of the fluid dispensing device 1 as illustrated in FIGS. 1-6 the spray delivery device 30 of the first type is assembled inside the accommodating space 36 of the housing 2. Here, the outlet 40 of the spray delivery device 30 is connected or fixed to the orifice 21. At least one of the outlet 40 and the orifice 21 comprise a jet nozzle 27 having a reduced diameter effective to atomize a streamlet of the fluid dispensed through the outlet 40.

With all examples as illustrated herein, the orifice 21 of the housing 2 of the fluid dispensing device is in alignment with the outlet 40, 140 of the spray delivery device 30, 130.

Even though not illustrated there might be further examples, wherein the orifice 21 provides a through opening for the outlet 40, 140 of the spray delivery device 30, 130. Here, the outlet 40, 140 may extend and reach through the orifice 21. With other examples, the orifice 21 may comprise a comparatively large opening in the housing 2, having a cross section that is larger in size than a cross-section of the spray delivery device 30, 130.

With a further example, the orifice 21 of the fluid dispensing device 1, 100 may be provided by the outlet 40, 140 of the spray delivery device 30, 130. Thus, the orifice 21 of the fluid dispensing device 1, 100 may coincide with the outlet 40, 140 of the spray delivery device 30, 130; and vice versa.

In the example of FIGS. 1-6, the outlet 40 is connected to or is integrally formed with the moveable part 35 of the spray delivery device 30. The spray delivery device 30 is mechanically engaged with a mechanical coupler 60. The mechanical coupler 60 is a component of the fluid dispensing device 1. The mechanical coupler 60 is engaged with a biasing member 50. The biasing member is presently configured as a compression spring having a first end 51 in abutment or engagement with the mechanical coupler 60 and further having a second end 52 opposite to the first end 51 that is in engagement or in abutment with the housing 2.

Figure 3:
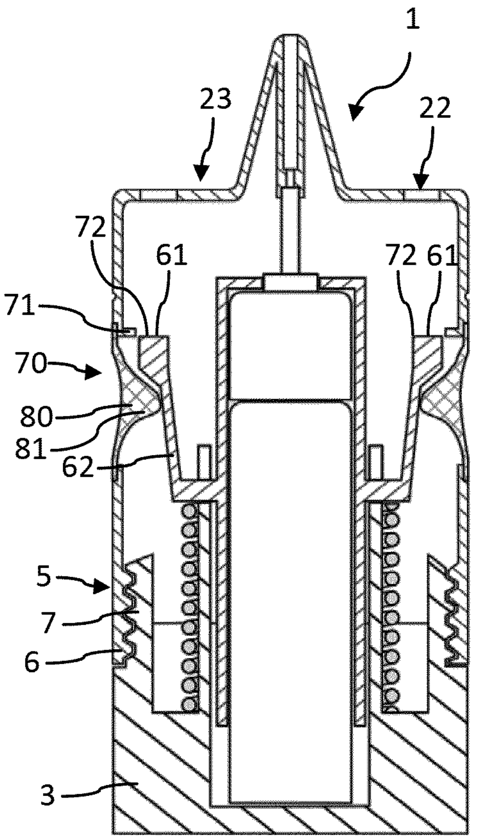
FIG. 3 shows the device of FIG. 2 after removal of a protective cap and after actuation of a trigger.
Figure 4:
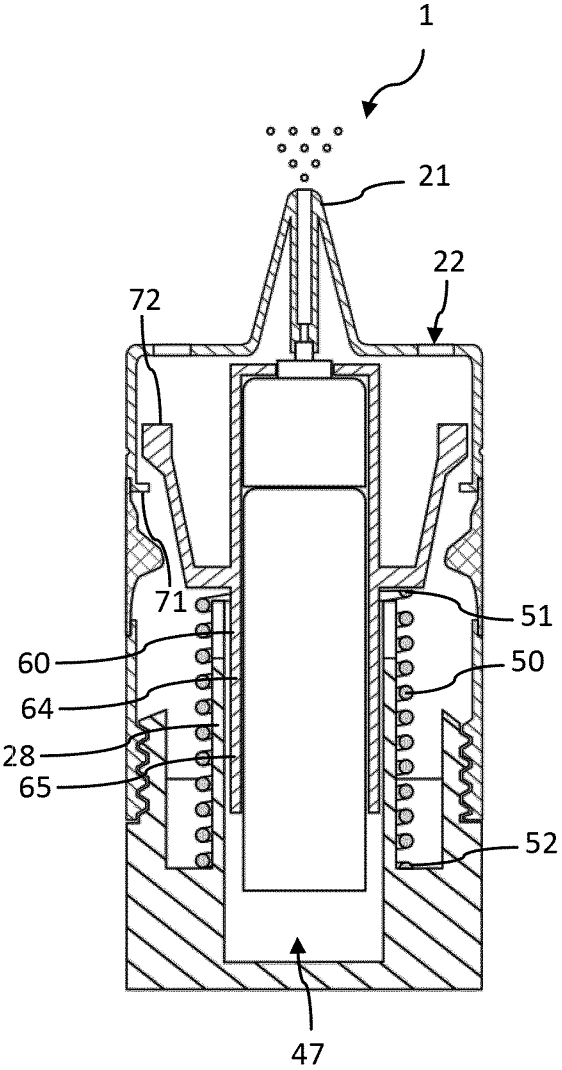
FIG. 4 shows the device of FIG. 3 during or after execution of a dispensing operation.
Figure 5:
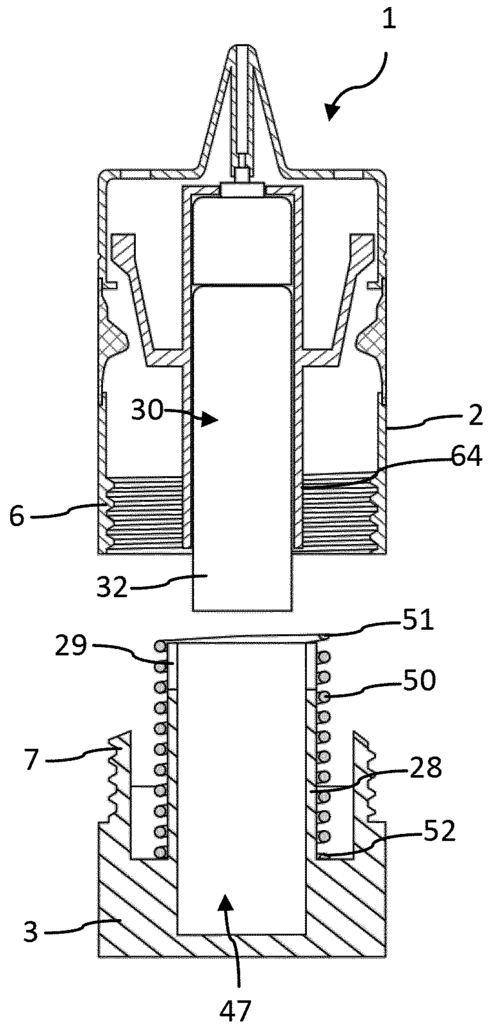
FIG. 5 shows the device with a closure detached from the housing.
Figure 6:
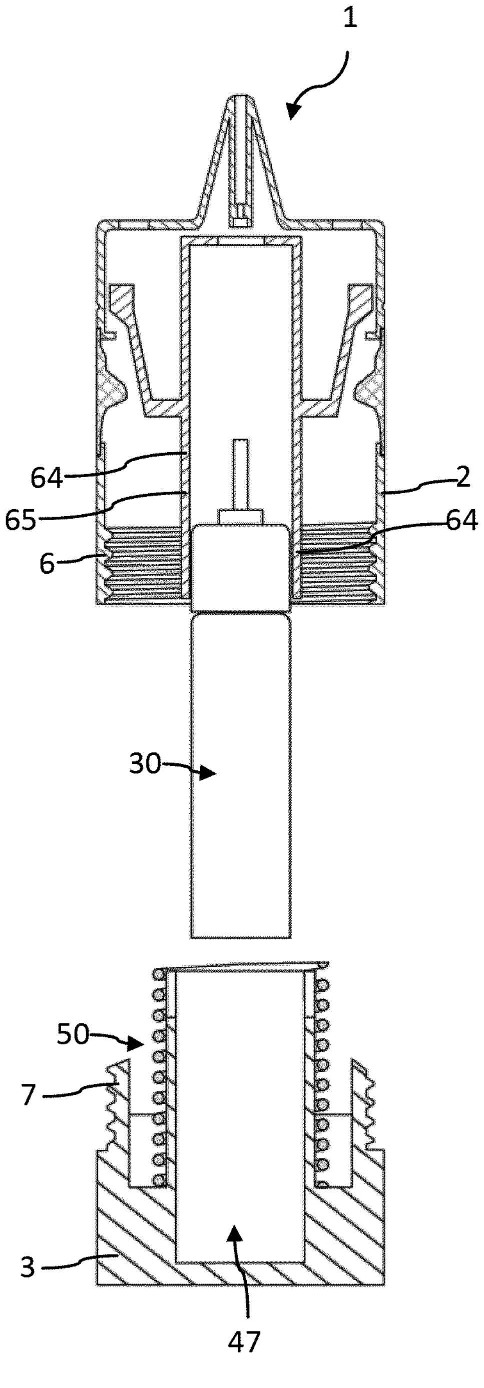
FIG. 6 shows the device during replacement of the spray delivery device.

Under the effect of the biasing member 50 the mechanical coupler 60 is displaceable from a preload position or biased position as illustrated in FIGS. 2 and 3 into an unload position as illustrated in FIGS. 4 to 6. The mechanical coupler 60 is displaceable from the unload position into the preload position against the action of the biasing member 50. In the presently illustrated example the biasing member 50 is located and arranged between a bottom of the housing 2 and a laterally extending struts 62 of the mechanical coupler 60. The container 32 and optionally also the base 45 of the spray delivery device 30 are fastened to or fixed to the mechanical coupler 60. Insofar, a movement of the mechanical coupler 60 relative to the housing 2 leads to a movement of the container 32 relative to the outlet 40 and thus to the dispensing of a dose of the fluid from the spray delivery device 30.

The mechanical coupler 60 is slidably displaceable inside the housing 2 in accordance to a longitudinal guiding structure 25. As illustrated in FIG. 2 the guiding structure 25 comprises at least two or even more shaft portions 28 extending parallel to a surface normal of a bottom of the housing 2. The shaft portions 28 may enclose the mechanical coupler 60. Therefore, the guiding structure 25 defines a longitudinal direction along which the mechanical coupler 60 is slidably displaceable relative to the housing 2 under and against the action of the biasing member 50. Instead of at least two or more shaft portions 28 the housing 2 may comprise a hollow sleeve extending into the accommodation space 26 and being configured and sized to slidably receive the mechanical coupler 60 therein.

The fluid dispensing device 10 further comprises an interlock 70 that is operable to retain the mechanical coupler 60 in the preload position as illustrated in FIGS. 2 and 3. The interlock 70 is further operable to retain the biasing member 50 in the pre-loaded state as illustrated in FIGS. 2 and 3. The fluid dispensing device 10 further comprises a trigger 80 that is operably engageable with the interlock 70 in order to release the interlock 70 and to enable unbiasing or unloading of the biasing member 50 for displacing the mechanical coupler 60 relative to the housing 2.

As shown in FIGS. 2-6 the mechanical coupler 60 comprises at least one strut 62 extending outwardly from the outer circumference of the, e.g. cylindrically-shaped mechanical coupler 60. The mechanical coupler 60 as illustrated in FIGS. 2-5 comprises at least two diametrically oppositely located struts 62 each of which extending through a slit or aperture provided in the guiding structure 25, hence in the shaft portions 28 of the guiding structure 25. The two slits 29 or grooves are provided near an upper free end of the shaft portions 28. They provide a well-defined longitudinal guiding of the mechanical coupler 60 relative to the housing 2. The struts 62 both comprise an abutment 61 facing towards a distal or upper end of the housing 2.

The interlock 70 comprises by a catch feature 71 provided on an inside of the housing 2 and a correspondingly or complementary-shaped snap feature 72 provided on the mechanical coupler 60. The snap feature 72 is provided on or at an end section of the strut 62 of the mechanical coupler 60. In an initial configuration and as illustrated in FIG. 2, the snap feature 72 of the mechanical coupler 60 is in direct abutment with the inwardly protruding catch feature 71 that is fixed to an inside of the housing 2. As it is apparent from a comparison of FIGS. 2 and 3, the struts 62 are elastically deformable such as to bring the catch feature 71 and the snap feature 72 out of mechanical engagement as illustrated in FIG. 3. Such a temporary deformation or pivoting of the snap feature 72 is obtained by depressing of the trigger 80.

The trigger 80 comprises an inwardly extending pin 81. The entire trigger 80 and/or its pin 81 may comprise a resilient material. Hence, the trigger 80 is depressible inwardly, hence into the interior of the accommodating space 26. The trigger 80 or both triggers 80 are operable to apply a respective inwardly directed force effect onto the interlock 70 and hence onto the inwardly deformable or inwardly pivotable struts 62 and are thus operable to bring the mutually corresponding snap features 72 and catch features 71 out of engagement. As long as the catch features 71 and the snap features 72 are in mutual abutment the respective engagement of the struts 62 with the housing 2 hinders and prevents a displacement of the mechanical coupler 60 towards the orifice 21.

As soon as the interlock 70 is released, e.g. by simultaneously depressing the oppositely located triggers 80, the respective interlocks 70 are released and the mechanical coupler 60 is allowed to become displaced towards the orifice 21 under the action of the relaxing biasing member 50 as illustrated in FIG. 4. As a consequence, a dose of the fluid is expelled through the orifice 21 due to the movement of the container 32 relative to the outlet 40.

Now and after a dose has been dispensed the protective cap 90 can be reassembled on the housing 2. The cup-shaped hollow cap 90 comprises a hollow interior 91 into which at least one longitudinal extension 92 extends. In the example as illustrated in FIGS. 2-6 the protective cap 90 comprises two longitudinally extending extensions 91 that may be configured as rods. The upper end or upper end face 23 of the housing 2 comprises at least one through opening 22. In the present example there are provided two through openings 22 each of which being longitudinally aligned with the position of the abutments 61 of the mechanical coupler 60.

As the protective cap 90 is reassembled onto the housing 2 the longitudinal extensions 92 enter the through openings 22 and extend through the through openings 22 until the longitudinal extensions 92 get in mechanical engagement, hence in direct abutment with the abutments 61 of the struts 62 of the mechanical coupler 60. Such an abutment configuration is obtained before the protective cap 90 reaches a closing position. The protective cap 90 is further displaceable or depressible downwardly, hence towards the bottom of the housing 2 thereby urging the mechanical coupler 60 towards the bottom of the housing 2 and against the action of the biasing member 50 until the initial configuration as illustrated in FIG. 2 has been reached, in which the protective cap 90 is in the closing position. Upon or prior to reaching the closing position as illustrated in FIG. 2 the interlock 70 automatically locks. The snap features 72 reengage with the catch features 71 and a spring-induced displacement of the mechanical coupler 60 is effectively prevented.

In this configuration the fluid dispensing device 1 can be stored until it is to be used for a proceeding dispensing action.

As it is apparent from a comparison of FIGS. 2 and 3 the trigger 80 is arranged flush in a sidewall 24 of the housing 2. An actuation of the triggers 80 as illustrated in FIG. 3 requires a depressing the triggers 80 further inwardly. The trigger or triggers 80 may be integrated into the sidewall 24. They may not protrude from the sidewall 24. This allows a rather smooth assembly of the protective cap 90 onto the housing 2 to such an extent, that a sidewall 94 of the protective cap 90 effectively and/or entirely covers the triggers 80.

In the closing position as illustrated in FIG. 2, the two triggers 80 are neither accessible nor depressible from outside. They are effectively inoperable as long as the protective cap 90 is in the closing position. Operation or actuation of the trigger 80 and hence a release of the interlock 70 requires a detachment or an opening of the protective cap 90. It is only then and as illustrated in FIGS. 3 and 4, that the triggers 80 become accessible such that they can be depressed or actuated by a user of the device. In this way, the fluid dispensing device 1 can be stored in a pre-loaded or pre-cocked state without a substantial danger of an inadvertent, uncontrolled or premature release of a dispensing action.

The protective cap 90 is held in place in the closing position as illustrated in FIG. 2 by means of at least one fastener. Here, an interior of the sidewall 94 of the protective cap comprises at least one fastening feature 95 configured to engage and to cooperate with a correspondingly-shaped counter-fastening feature 96 provided on an outside surface of the housing 2. Typically, one of the fastening feature 95 and the counter-fastening feature 96 comprises a protrusion configured to engage with a correspondingly or complementary-shaped recess of the other one of the fastening feature 95 and the counter-fastening feature 96. The fastening feature 95 and the counter-fastening feature 96 are configured to form at least one of a positive connection and a frictional engagement. They may comprise mutually corresponding snap- or catch features.

With the example as illustrated in FIGS. 2-6 the housing 2 is detachably connectable with a closure 3. The closure 3 forms a bottom 4 of the housing 2. In the illustrated example the closure 3 forms or constitutes a cup-shaped receptacle for the container 32 of the spray delivery device 30. A sidewall of the closure 3 comprises a threaded portion 7 correspondingly-shaped to a threaded portion 6 of the housing 2. In this way the closure 3 can be detached from the housing 2 by a screwing motion with regard to a longitudinal central axis of the housing 2 as an axis of rotation.

The closure 3 comprises the inwardly extending shaft portion 28. The shaft portion 28 forms a receptacle for the mechanical coupler 60. The mechanical coupler 60 may be implemented as a carrier 64 that is connected and/or mechanically engaged with the spray delivery device 30 or at least the container 32 thereof.

The carrier 64 is provided with the struts 62. The mechanical biasing member 50, hence the compression spring is located radially outside the shaft portion 28. The second end 52 of the mechanical biasing member 50 is in longitudinal abutment with an inside facing bottom section of the bottom 4. The first end 51 of the mechanical biasing member 50 is in abutment with a side of the laterally extending struts 62 facing towards the bottom 4.

In the illustration of FIGS. 2 and 3 the carrier 64 and hence the barrel or sleeve 65 of the carrier connected to or in engagement with the spray delivery device 30 is in a biased position or in a first longitudinal position relative to the housing 2. Release of the interlock 70 and/or actuation of the trigger 80 induces a longitudinal displacement of the carrier 64 until it arrives in the unbiased position as illustrated in FIG. 4. Here, the carrier 64 and hence the mechanical coupler 60 is in a second longitudinal position relative to the housing 2. In the biased position and as long as the carrier 64 is in the first longitudinal position as illustrated in FIGS. 2 and 3 the carrier 64 is rotationally locked to the closure 3. The rotational lock is provided by the laterally extending struts 62 extending through the elongated or slitted apertures 29 extending in longitudinal direction in the shaft portion 28 of the closure 3.

Moreover, the laterally outwardly located portions of the struts 62, in particular the upper ends of the struts 62 may be in a splined engagement with an inside of the sidewall of the housing 2. In this way the mechanical coupler 60 and hence the carrier 64 is rotationally locked to the housing 2 but is free to slide relative to the housing 2 with regard to the longitudinal direction of the housing.

Accordingly and as the carrier 64 is in the biased position or in the first longitudinal position as illustrated in FIGS. 2 and 3 the shaft portion 28 and hence the closure 3 is and remains rotationally locked to the mechanical coupler 60 and/or to the carrier 64, which in turn is and remains rotationally locked to the housing 2.

It is only when reaching the second longitudinal position or the unbiased position as illustrated in FIG. 4 that the struts 62 are out of engagement with the aperture 29 in the shaft portion 28. Accordingly, the shaft portion 28 and hence the entire closure 3 is free to rotate relative to the mechanical coupler 60 and the carrier 64 and hence also relative to the housing 2. Accordingly, and only in the unbiased position of the carrier 64 the closure 3 can be moved from the closed position towards the open position. In particular, the closure 3 can be unscrewed from the housing 2 and the threaded connection 5 between the closure 3 and the housing 2 can be disconnected.

Instead of a threaded connection as illustrated in FIGS. 2-6 the closure 3 may be connected to the housing 2 by way of a bayonet joint.

In either way the fluid dispensing device 1 comprises a safety arrangement 10 that is constituted by the mechanical engagement of the housing 2, the carrier 64 and the closure 3.

The carrier 64 may thus belong to the safety arrangement 10 or may contribute to the functionality of the safety arrangement 10.

Once the closure 3 is disconnected from the housing 2 at least the container 32 of the spray delivery device 30 is accessible from outside the housing 2. As shown in FIG. 6 the container 32 or the entirety of the spray delivery device 30 can be withdrawn or taken out of the housing 2. It can be then replaced by a new spray delivery device 30 or container 32.

When the closure 3 is disconnected or detached from the housing 2 the mechanical biasing member 50 is assembled and/or attached to the closure 3 as illustrated in FIGS. 5 and 6. Here, the second end 52 of the biasing member 50 may be connected or fixed to the interior of the closure 3. With other examples the biasing member 50 may be attached to the carrier 64 and/or to the mechanical coupler 60. Here, the first end 51 of the mechanical biasing member 50 may be connected to the mechanical coupler 60 or to the carrier 64.

The spray delivery device 60 may be frictionally engaged with the carrier 64. With some examples the spray delivery device 30 and the carrier 64 are mutually engaged by a positive fit.

Figure 7:
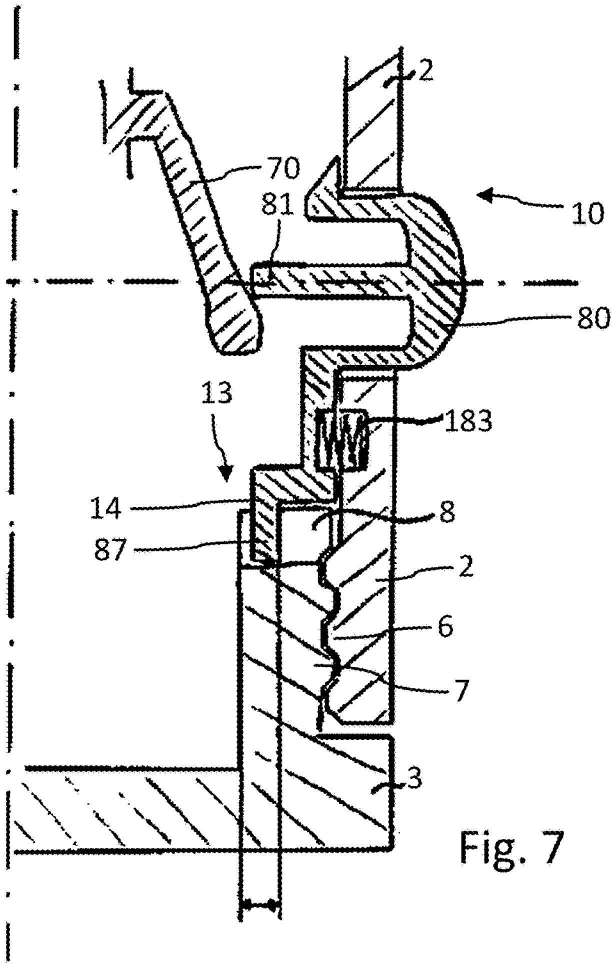
FIG. 7 shows another example of a safety arrangement of the fluid dispensing device.
Figure 8:
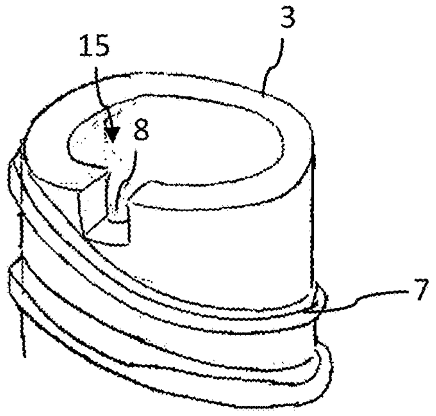
FIG. 8 is a schematic illustration of an upper portion of the closure of the device according to FIG. 7.
Figure 9:
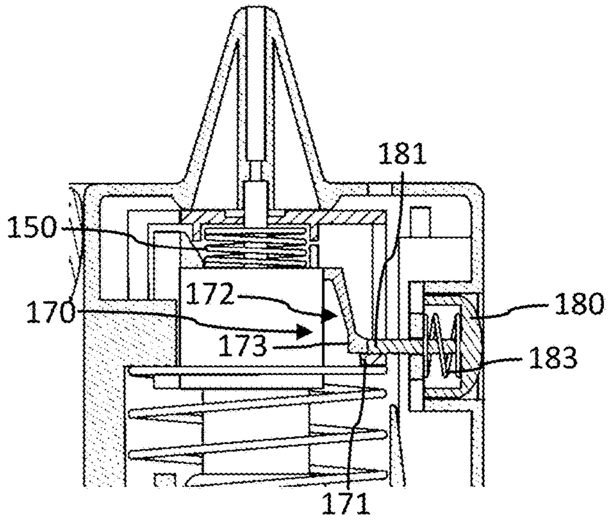
FIG. 9 shows one example of a trigger of the fluid dispensing device in greater detail.

In the illustrations of FIG. 7-9 another example of a safety arrangement 10 is illustrated. Here, the safety arrangement 10 is configured to prevent a movement of the closure 3 from the closed position towards the open position as long as the mechanical biasing member 50 is in the pre-loaded state. For transferring the mechanical biasing member 50 (not illustrated) into the unloaded state it is only necessary to depress or to actuate the trigger 80. The trigger 80 is provided with a spring 183 connected with one end to the trigger 80 and connected with the other end to the housing 2. The spring 183 is configured to keep the trigger 80 in the idle position as illustrated in FIG. 7. The trigger 80 is further engageable with the interlock 70 as indicated in FIG. 7. Depressing of the trigger 80 leads to an unlocking of the interlock 170 in a way as, e.g. described in greater detail below with respect to FIGS. 37-39.

In the example of FIGS. 7 and 8 the closure 3 comprises a threaded portion 7, e.g. in form of an outer thread. The threaded portion 7 is configured to mate with a complimentary-shaped threaded portion 6 on an inside of a sidewall of the housing 2. In the closed position of the closure 3 as illustrated in FIG. 7 an extension 87 of the trigger 87 is located in a slit or groove 8 of a sidewall of the closure 3. Since the trigger 80 is fixed to the housing 2 with regard to the tangential or circumferential direction of the housing the extension 87 serves as a latch 14 located in a correspondingly-shaped latch keeper 15 of the closure 3.

The latch 14 is formed by the extension 87. The latch keeper 115 is formed by the slit or recess in the sidewall of the closure 3. As long as the latch 14 is engaged with the correspondingly-shaped latch keeper 15 a closure lock 13 formed by the latch 14 and the latch keeper 15 is in a locked state as illustrated in FIG. 7.

Transferring of the closure lock 13 into an unlocked state requires a displacement of the trigger 80 and hence of the latch 14 and the extension 87 inwardly relative to the latch keeper 15. By depressing the trigger 80 into the housing 2 the latch 14 is displaced relative to the latch keeper 15 and disengages from the latch keeper 15. In such a configuration (not illustrated) and while the trigger 80 is and remains depressed or actuated the closure lock 13 is unlocked and the closure 3 can be rotated relative to the housing 2 for unscrewing or for releasing the threaded connection 5 between the closure 3 and the housing 2.

In FIG. 9 another implementation of a trigger 180 is illustrated. Here, the trigger 180 comprises a pin 181 engageable with a snap feature 172 comprising a resilient member 173. By depressing the trigger 180 inwardly against the action of a trigger spring 183 the catch feature 171 of the interlock 170 is displaced or deformed by the pin 181. It can be released by way of which the mechanical energy stored in the mechanical biasing member 150 will be released. Even though not illustrated in greater detail the safety arrangement 10 as illustrated in FIG. 7 can be correspondingly implemented with the example of the trigger 180 and the interlock 170 as illustrated in FIG. 9. Further details of the mutual engagement between the trigger 180 and the interlock 170 as shown in FIG. 9 will be apparent from the below description of FIGS. 36-42.

With the further example of the fluid dispensing device 1 as illustrated in FIGS. 10-16 the closure 3 is also detachably connected to the housing 2. But here and contrary to the example of FIGS. 2-6 the mechanical biasing member 50 is entirely located inside a compartment 47 of the closure. The compartment 47 is confined by a bottom of the closure and by an oppositely located partition wall 49. The partition wall 49 forms an upper end of the compartment 47. Inside the compartment 47 there is further arranged a pressure piece 48. The pressure piece 48 may comprise a pressure plate. A lower side of the pressure piece 48 is in abutment with the first end 51 of the mechanical biasing member 50. The second end 52 of the biasing member 50 is in abutment with an inside facing portion of the bottom of the closure 3.

The partition wall 49 is further provided with a through opening 46. The through opening is sized to receive at least the container 30 of the spray delivery device 30. In the illustrated example the through opening 46 is sized to receive the mechanical coupler 60 and hence the carrier 64 that is mechanically fixed to the spray delivery device 30.

Figure 10:
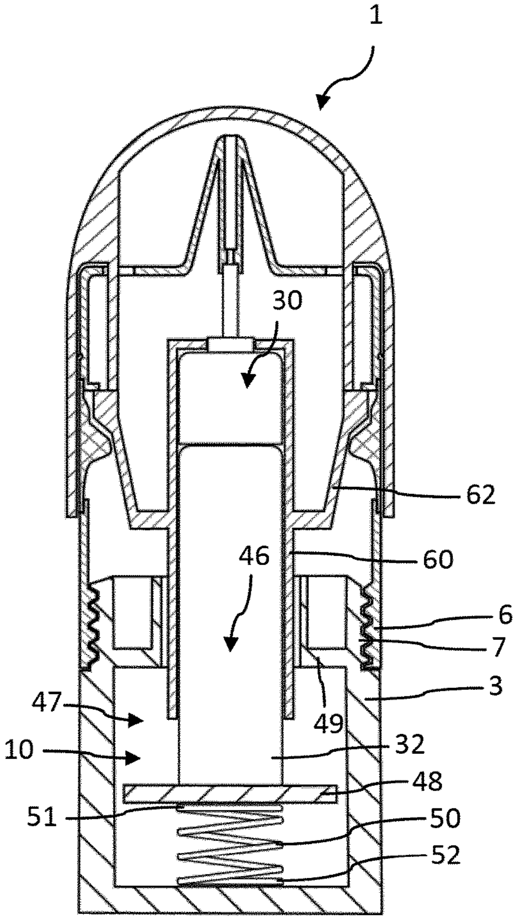
FIG. 10 shows another example of the fluid dispensing device in an initial configuration.
Figure 11:
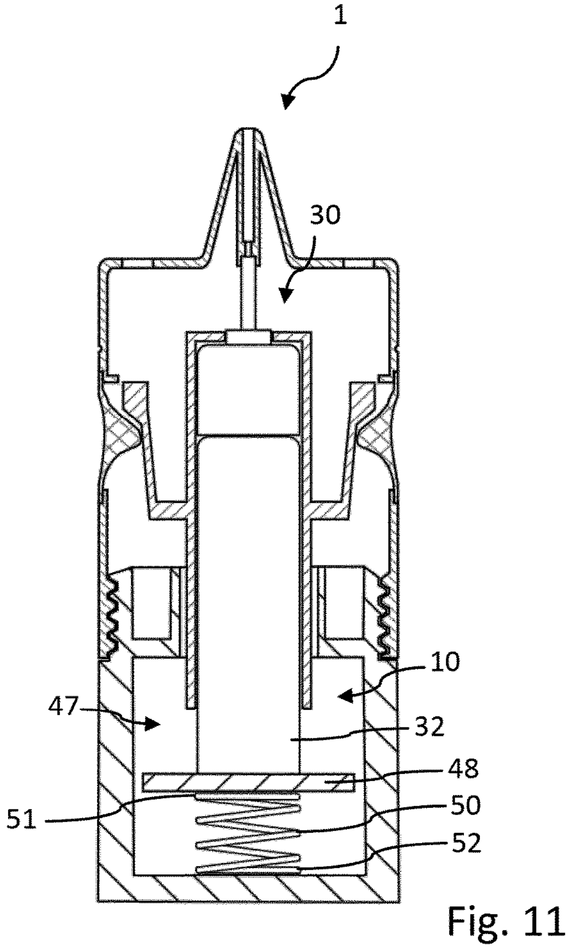
FIG. 11 shows the device of FIG. 10 with the protective cap removed.
Figure 12:
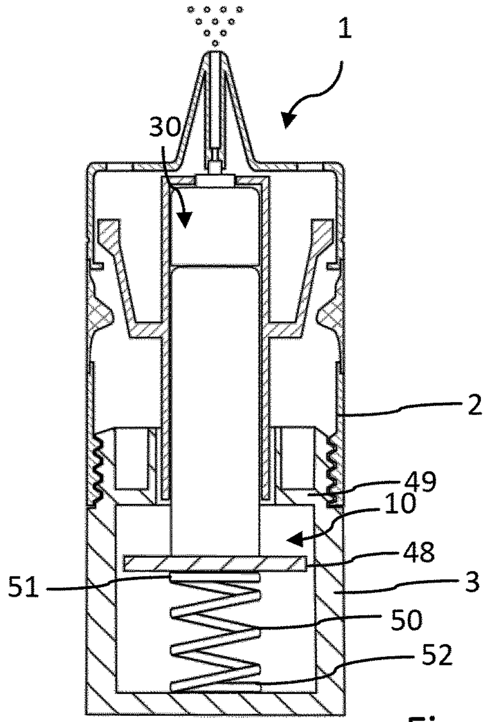
FIG. 12 shows the device of FIG. 10 during or after execution of a dispensing operation.
Figure 13:
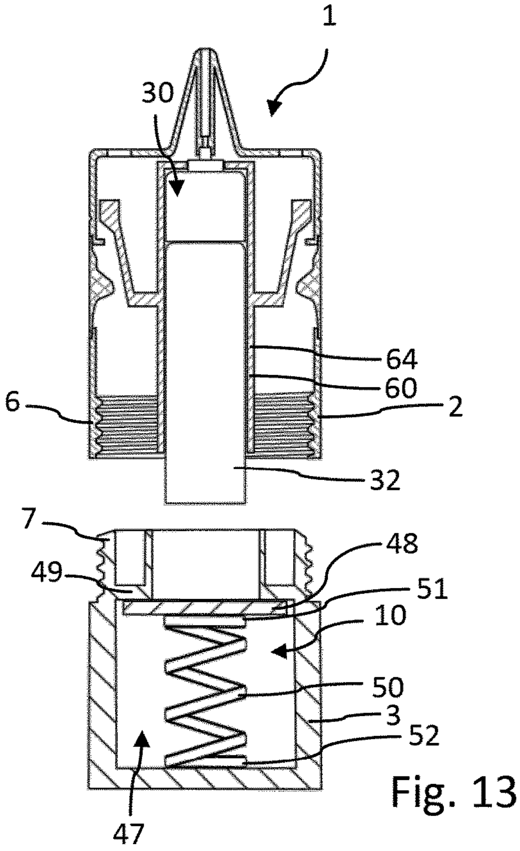
FIG. 13 shows of the device of FIG. 12 after or during detachment of the closure.

The safety arrangement 10 as illustrated in FIGS. 10-16 is configured and operable to release at least a portion of the mechanical energy of the pre-loaded mechanical biasing member 50 during and through a movement of the closure 3 from the closed position as illustrated in FIGS. 10-12 towards the open or released position as shown in FIGS. 13-16.

The closure 3 and the housing 2 may be interconnectable by a threaded connection 5 or by a respective bayonet joint that requires a rotation of the closure 3 relative to the housing 2 with respect to a longitudinal axis. Here, the elongation of the mechanical biasing member 50 is substantially parallel to the longitudinal axis. When the mechanical biasing member 50 is in the pre-loaded state the closure 3 can be rotated relative to the housing 2 so as to detach the closure 3 from the housing 2. During such a helical motion as governed by the threaded connection 5 the closure 3 is moved away from the housing 2 in a direction that leads to a relaxing of the pre-loaded mechanical biasing member 50.

Figure 14:
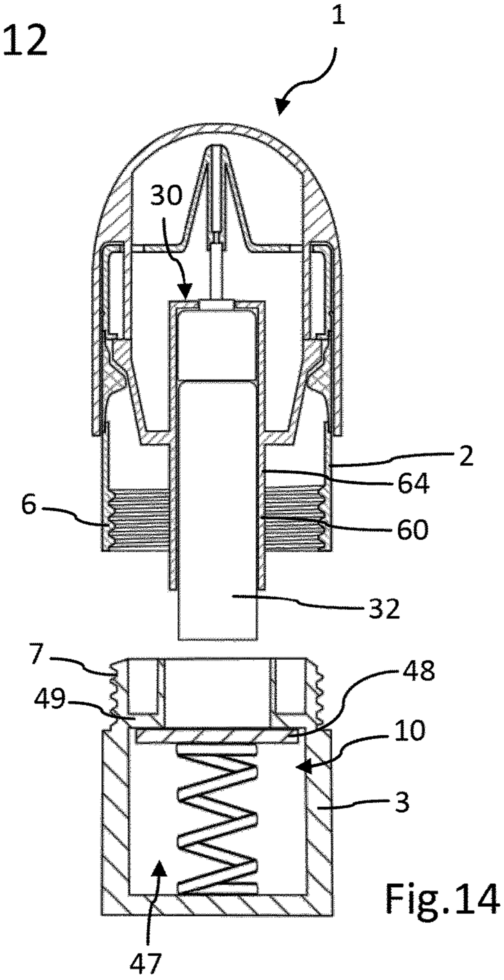
FIG. 14 shows the device according to FIG. 13 with the protective cap in a closing position.
Figure 15:
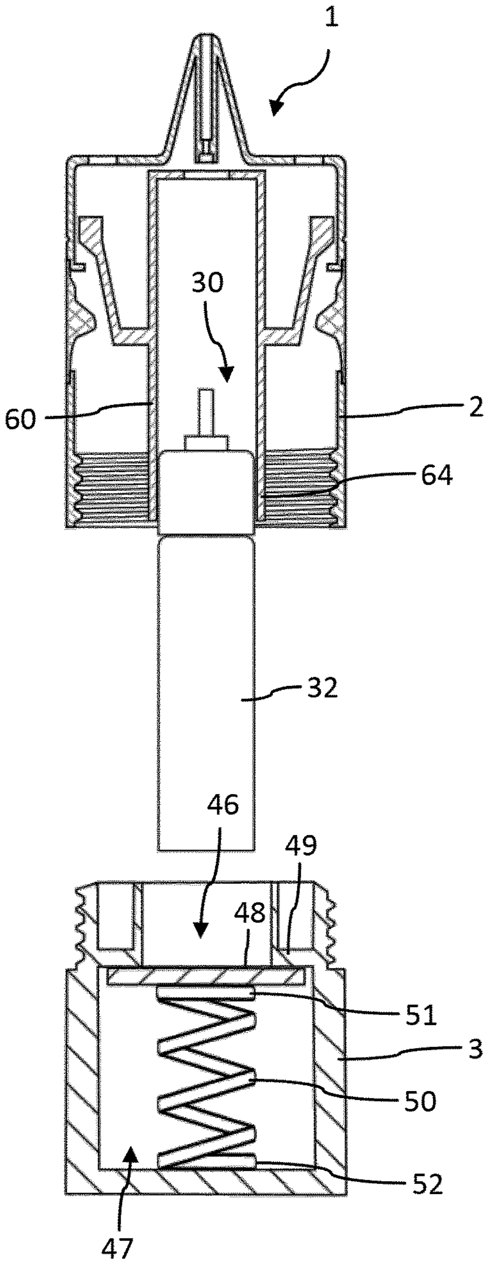
FIG. 15 shows the device of FIG. 13 during replacement of the spray delivery device.
Figure 16:
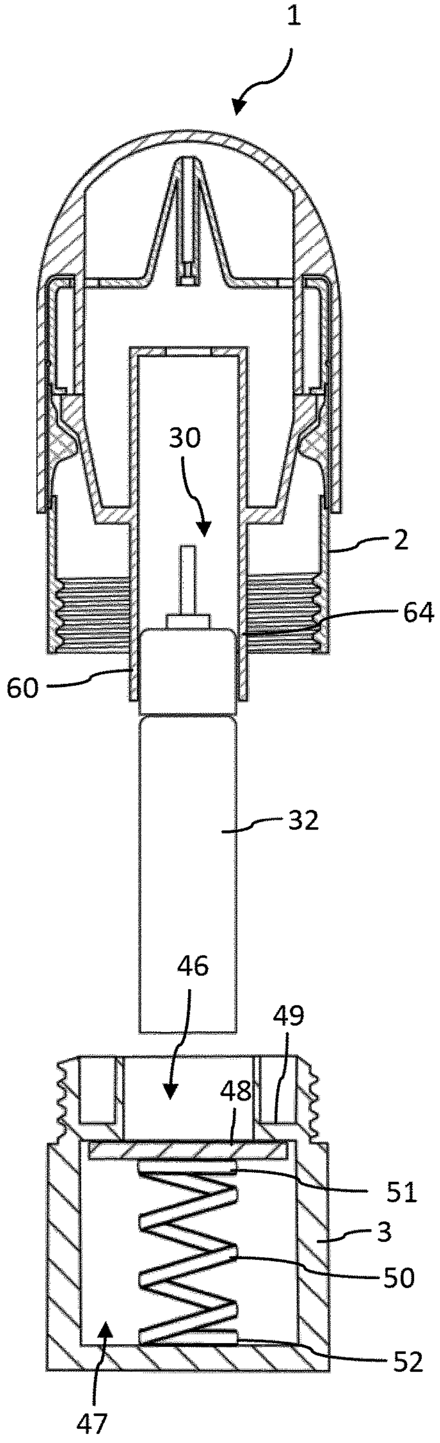
FIG. 16 shows the device according to FIG. 14 during replacement of the spray delivery device.
Figure 17:
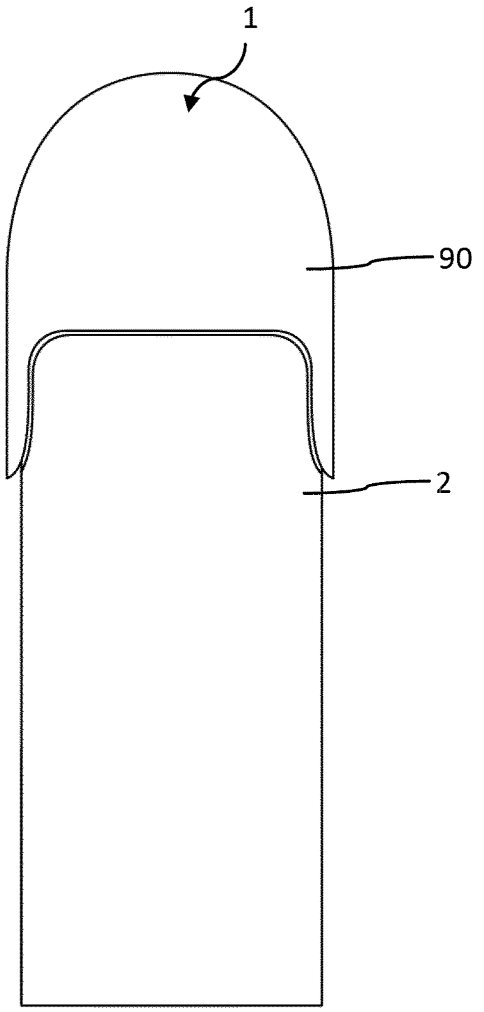
FIG. 17 is a front view of another example of a fluid dispensing device.
Figure 18:
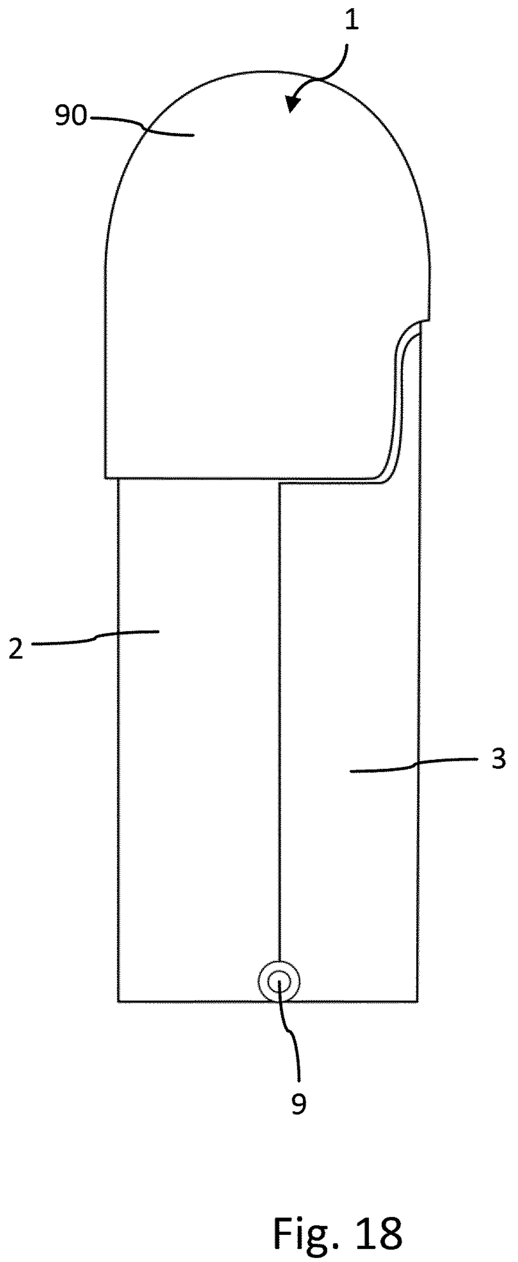
FIG. 18 is a side view of the device of FIG. 17.

During and through a movement of the closure 3 from the closed position as shown in FIGS. 10-12 towards the open position as shown in FIGS. 13-16 the mechanical biasing member 50 is subject to mechanical energy dissipation and serves to urge the pressure piece 48 towards the partition wall 49 as shown in FIGS. 13-16. Even when the closure 3 is disconnected from the housing 2 while the mechanical biasing member 50 is and remains in the pre-loaded state as illustrated in FIGS. 14 and 16 the mechanical energy stored in the mechanical biasing member 50 cannot dissipate in an uncontrolled way.

At most, the pressure piece 48 is urged into abutment with the partition wall 49. The biasing member 50 cannot disassemble in a self-actuated way from the closure 3 but remains confined inside the compartment 47. As it is apparent from FIGS. 15 and 16 the spray delivery device 30 is replaceable by another spray delivery device in any configuration of the carrier 64. When the closure 3 is detached from the housing 2 at least a lower end of the container 32 can be gripped and withdrawn out of the carrier 64 or mechanical coupler 60. After assembly of another spray delivery device 30 into the carrier 64 or into the mechanical coupler 60 the fluid dispensing device 1 can be reassembled, thereby at least partially biasing the mechanical biasing member 50.

In the further example of FIGS. 17-25 the housing 2 of the fluid dispensing device 1 comprises a closure 3 that is and remains undetachably connected with the housing 2. As it is apparent from a comparison of FIGS. 21 and 24 the closure 3 is pivotally connected to the housing 2. A hinge 9 connecting the housing 2 and the closure 3 is for example located near a bottom end of the housing 2 that is located opposite to the orifice 21.

Figure 21:
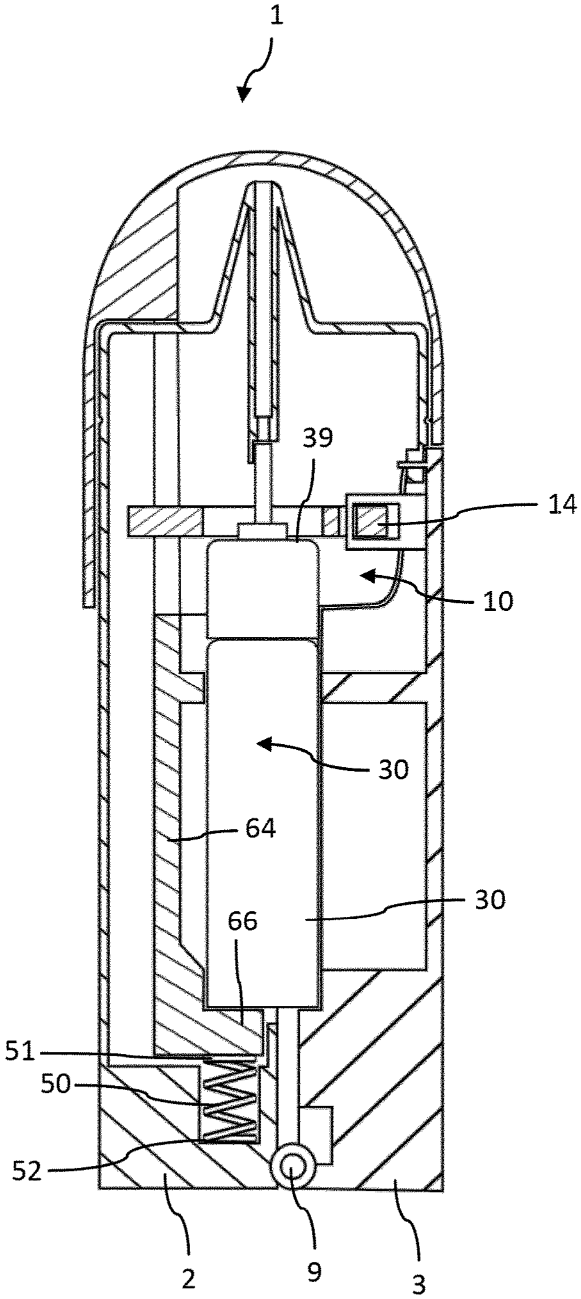
FIG. 21 is a cross-section through the device of FIG. 19 rotated by 90°.

Here, the carrier 64 is configured to support and/or to receive at least a portion of the spray delivery device 30. The carrier 64 comprises a bottom 66 that is in longitudinal abutment with a bottom portion of the spray delivery device 30 and/or with a bottom portion of the container 32 as illustrated in FIG. 21. An opposite and lower end of the bottom 66 of the carrier 64 is in abutment with the first end 51 of the mechanical biasing member 50. An opposite second end 52 of the mechanical biasing member 50 is in abutment with the housing 2.

In effect, the entire spray delivery device 30 is displaceable or slidable relative to the housing 2 under the action of the mechanical biasing member 50.

Figure 19:
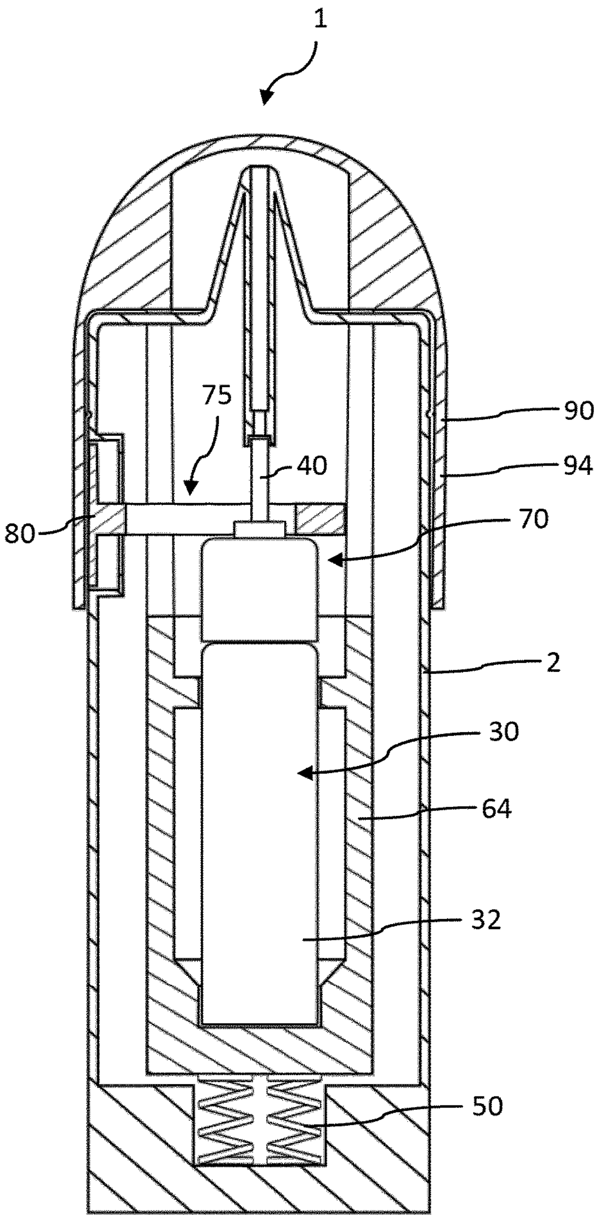
FIG. 19 is a cross-section through the device of FIG. 17.
Figure 22:
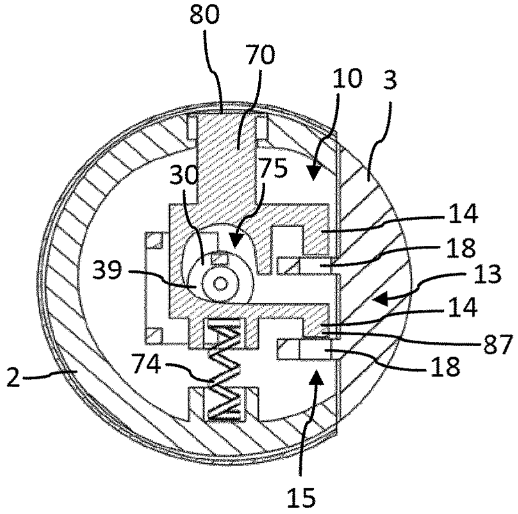
FIG. 22 is a transverse cross-section through the device of FIG. 17 with the trigger in an idle position.

As best seen in FIGS. 19 and 22 the interlock 70 comprises a slider that is moveable relative to the housing in a transverse direction against the action of a spring 74. The spring 74 is configured to keep the interlock 70 in the locked state as illustrated in FIGS. 19 and 22. In the locked state the interlock 70 is in abutment with a shoulder portion 39 near the outlet 40 of the spray delivery device 30. As illustrated in FIG. 22 the interlock 70 comprises an aperture 75 sized to receive the cross-section of the spray delivery device 30. However, the spring 74 urges the interlock 70 in transverse direction with regard to the elongation of the spray delivery device 30 and misaligns the aperture 75 with respect to a lateral position of the spray delivery device 30. Accordingly, a side edge of the aperture 75 is in abutment with a longitudinally facing shoulder portion 39 of the spray delivery device 30. In this way the spray delivery device 30 and the entire carrier 64 are kept and locked in the biased position.

Figure 20:
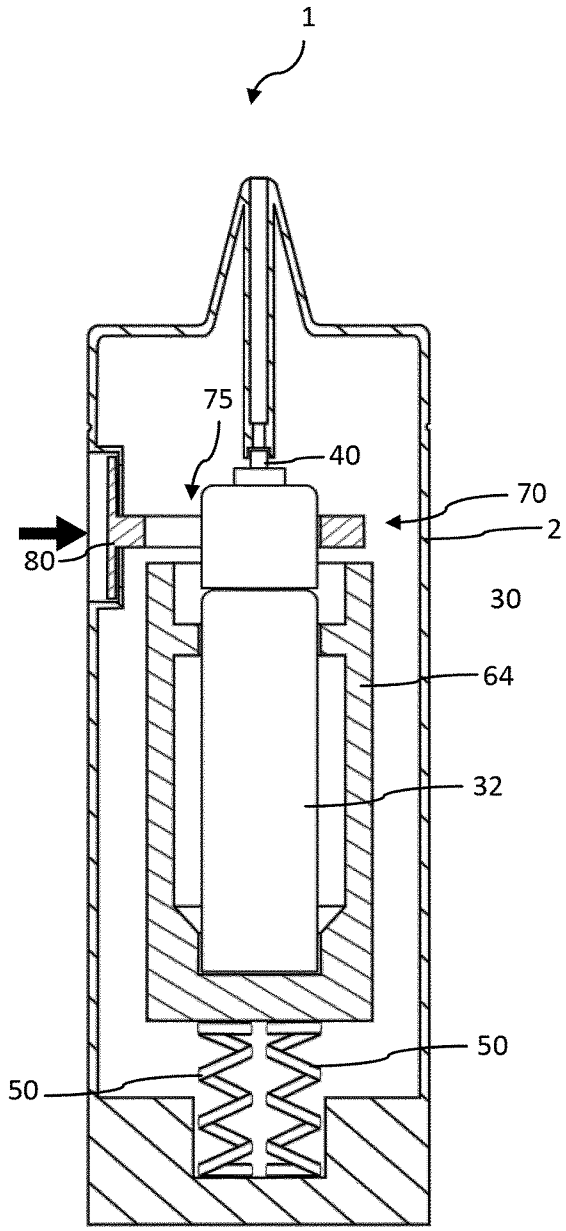
FIG. 20 shows the device of FIG. 19 after actuation of the trigger.
Figure 23:
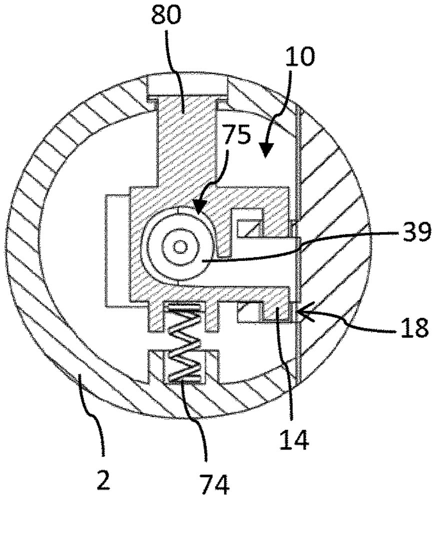
FIG. 23 is a cross-section according to FIG. 22 with the trigger in the actuated position.

The trigger 80, which is integrally formed with the interlock 70, is depressible in transverse direction such that the aperture 75 aligns in longitudinal direction with the circumference of the spray delivery device 30. As illustrated in FIGS. 20 and 23 and as soon as the aperture 75 aligns with the spray delivery device 30 the spray delivery device 30 is capable to enter or to extend through the aperture 75. Such a longitudinal displacement is governed by the unloading mechanical biasing member 50.

Accordingly, the carrier 65 is moved together with the spray delivery device 30 towards the orifice 21. In the actuated position of the trigger 80 and in the unlocked state of the interlock 70, as illustrated in FIGS. 20 and 23, laterally protruding extensions 87 of the trigger 80 enter correspondingly-shaped recesses 18 of the closure 3 provided near an upper end of the closure 3. The recesses 18 serve as a latch keeper 15 to receive a correspondingly-shaped latch 14 provided by the extension 87 of the trigger 80. When the extensions 87 are engaged with the recesses of the closure 3 the closure 3 cannot be pivoted into the open position. It is hence locked to the housing 2. Accordingly, the closure lock 13 constituted by the extensions 87 to engage with the recesses 18 of the closure serves to lock the closure 3 in the closed position as long as the trigger 80 is depressed.

Figure 24:
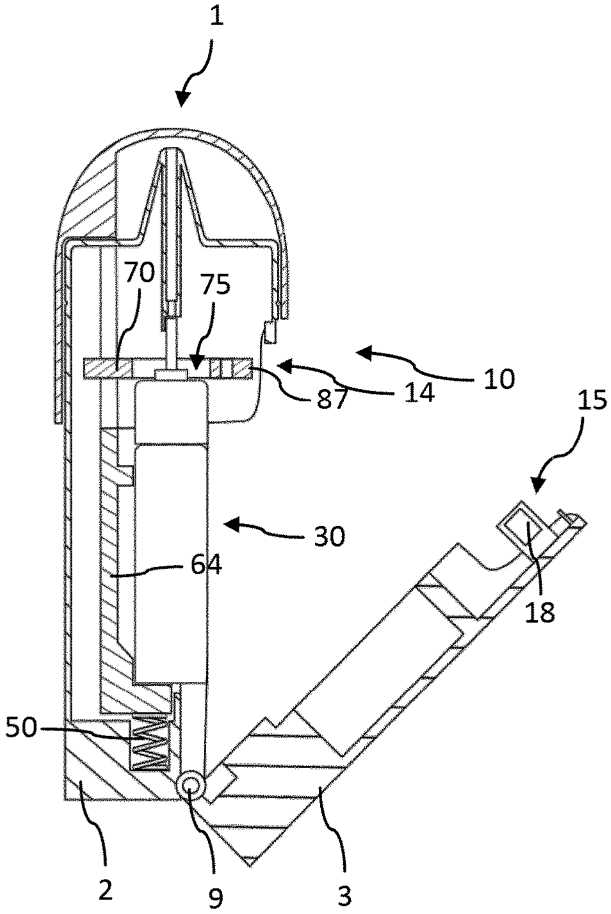
FIG. 24 is a cross-section according to FIG. 21 with the closure in the open position and FIG. 25 shows the configuration of FIG. 24 during replacement of the spray delivery device.
Figure 25:
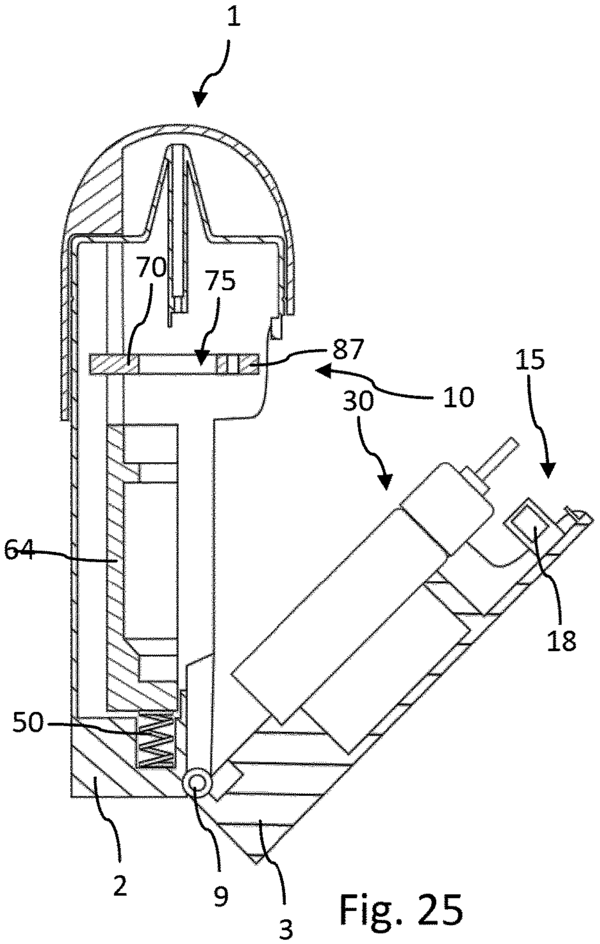

With another example not illustrated here it is also conceivable, that the closure lock 13 is locked in the configuration of FIG. 22, i.e. when the trigger 80 is in the idle position and when the interlock 70 is in the locked state. When the trigger 80 has been actuated and hence when the interlock 70 is in the unlocked state as illustrated in FIGS. 20 and 23 the closure lock 13 may be in the unlocked state. Then, the extensions 87 may disengage from the recesses 18 thus enabling opening of the closure 3 and replacing the spray delivery device 30 as illustrated in FIGS. 24 and 25.

With the example of FIGS. 17-25 transferring of the mechanical biasing member 50 into the preloaded state may be obtained by closing the protective cap 90. Also here and as described in connection with FIG. 2 the protective cap 90 may comprise inwardly extending extensions 92 configured to engage with the carrier 64 to transfer the carrier 64 from the unbiased position into the biased position against the action of the mechanical biasing member 50. The interlock 70 will reengage with the shoulder portion 39 under the action of the spring 74.

With this example the safety arrangement 10 is configured to prevent a movement of the closure 3 from the closed position towards the open position as long as the trigger 80 is in the actuated state and/or as long as the interlock 70 is in the unlocked state.

In FIGS. 26-47 further examples of fluid dispensing devices 100 are illustrated that make use of a spray delivery device 130 of the second type. Here, the container 132 is fixed inside a housing 102 of the fluid dispensing device 100 whereas the moveable part 138 of the spray delivery device 130 is subject to a displacement or movement relative to the housing 102. As it will become apparent, the outlet 140 of the spray delivery device 130 is immobile relative to the container 132. It may be fixed to the container 132. Rather, the moveable part 135 is displaceable relative to both, the container 132 and the outlet 140. Also here, the outlet 140 is fixed to the housing 102. It is in fluid engagement with an orifice 121 provided at an upper end of the housing.

Figure 26:
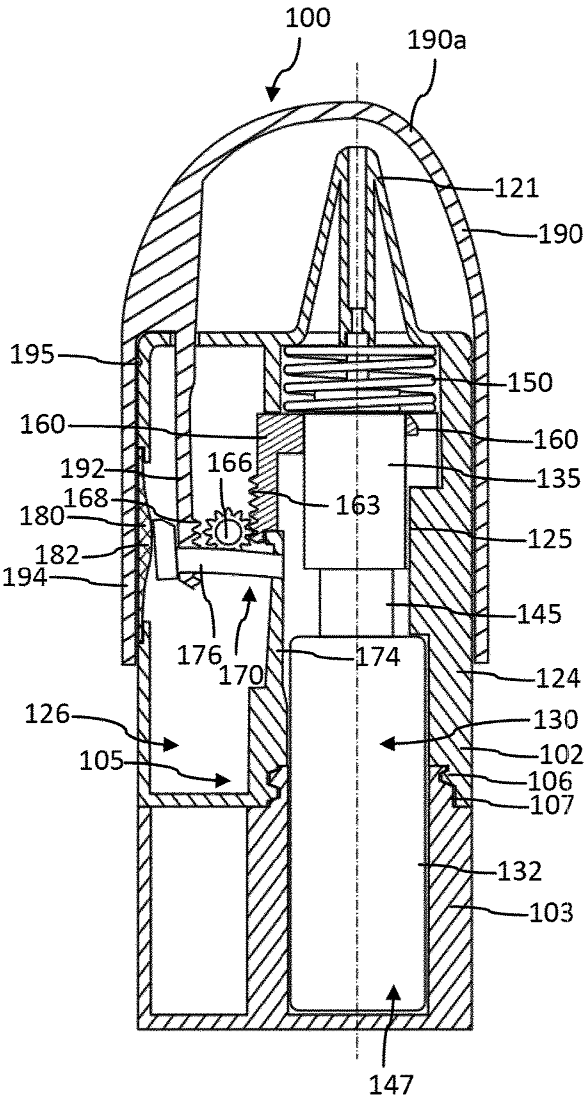
FIG. 26 is a longitudinal cross-section through another example of a fluid dispensing device with the protective cap in the closing position.

The upper end of the housing 102, hence an end face 123 equipped with the orifice 121 is configured to be entirely covered by a detachable protective cap 190. The protective cap 190 comprises a cap portion 190*a* that is configured to cover and set or to obstruct the orifice or 121 of the prior delivery device 130 when the protective cap 190 is in the closing position. The cap 190 can be held in a closing position as illustrated in FIG. 26 by mutually corresponding fastening features 195 and 196 of the protective cap 190 and of the housing 102, respectively. The fastening features and counter-fastening features 195, 196 comprise one of a protrusion and a recess e.g. to provide a snap fit engagement of the protective cap 190 and the housing 102.

As illustrated in FIGS. 26-29 the moveable part 135 of the spray delivery device 130 is connected and fixed to the mechanical coupler 160. The mechanical coupler 160 is slidably displaceable inside the housing 102 by means of a guiding structure 125. The mechanical coupler 160 is in engagement with the biasing member 150. One end 151 of the biasing member 150 is in abutment with an inside facing portion of the housing 102 and a second end 152 of the biasing member 150 is in engagement or in abutment with the mechanical coupler 160. In this way, the mechanical coupler 160 and hence the moveable part 135 attached thereto can be displaced relative to the housing 102 against the action of the biasing member 150.

In an initial configuration as illustrated in FIG. 26 the mechanical coupler 160 is in a preload position. It is kept in the preload position by an activated interlock 170. The interlock 170 comprises a resilient member 173, e.g. in form of a deformable leg 174 attached to or integrally formed with the housing 102. The leg 174 is provided with a catch feature 171 to engage with a snap feature 172 of the mechanical coupler 160. In this way, the mechanical coupler 160 is hindered to move towards the bottom of the housing 102 under the effect of the relaxing biasing member 150. Also here, the biasing member 150 is implemented as a helically wound compression spring.

The trigger 180 is integrated or is mounted flush with a sidewall 124 of the housing 102. It may comprise a resiliently depressible knob or button 182. Inside the housing 102 and hence in the accommodating space 126 there is further provided a bridging piece 176 that provides a mechanical link between the trigger 180 and the leg 174 and hence between the trigger 180 and the interlock 170. The bridging piece 176 may also belong to the trigger 180 or may be integrally formed with the trigger 180. The bridging piece 176 comprises one end in engagement or abutment with an inside portion of the trigger 180. The bridging piece 176 comprises an opposite second end that is in abutment or in engagement with the leg 174 or with a resilient member 173 of the interlock 170.

Figure 27:
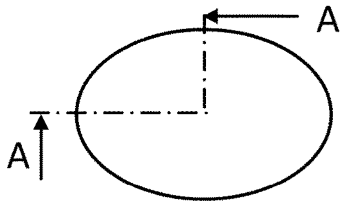
FIG. 27 shows the device of FIG. 26 during or after actuation of the trigger.
Figure 27:
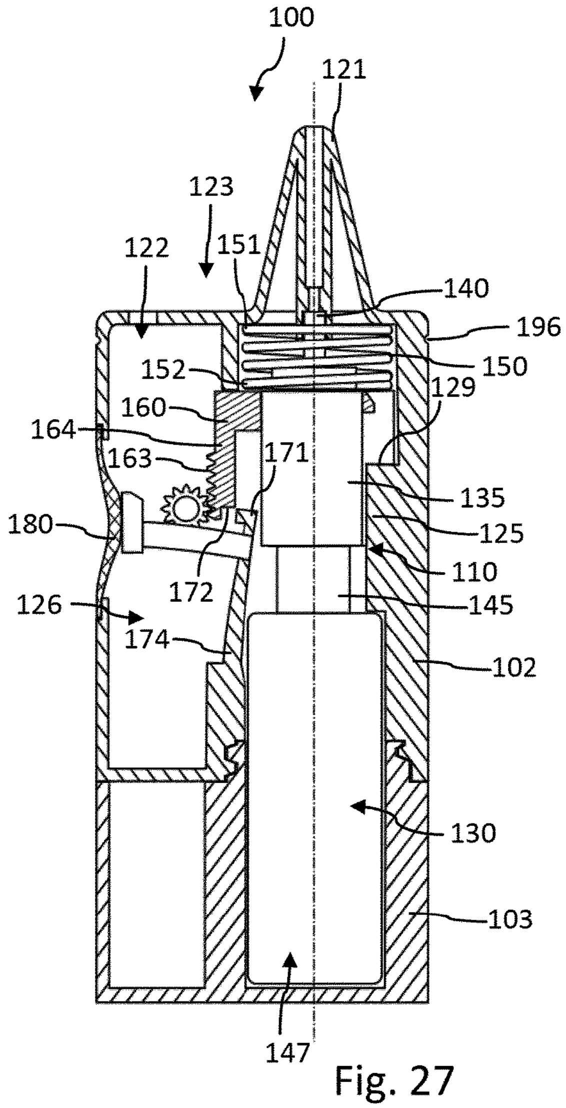
Figure 28:
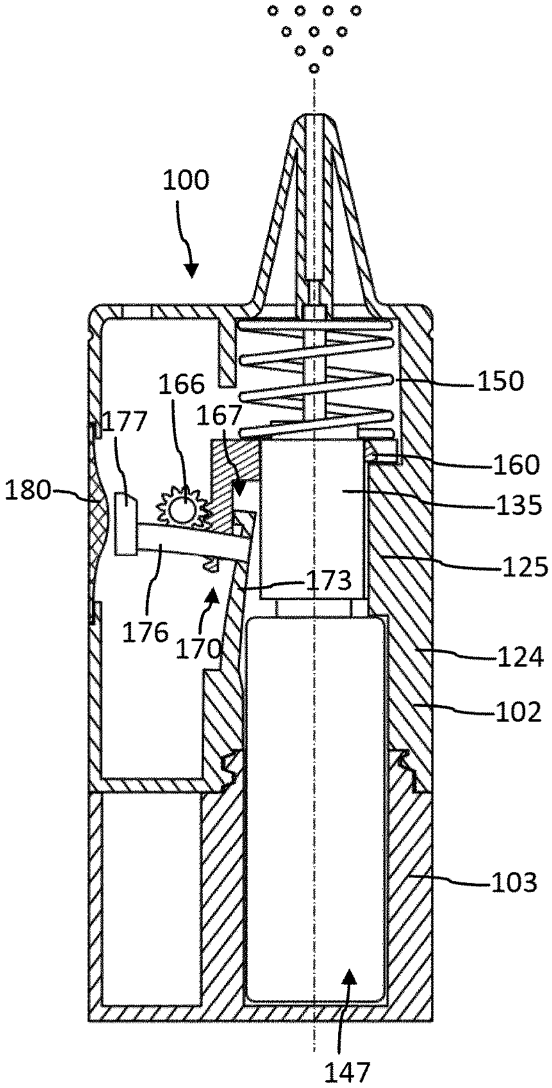
FIG. 28 shows the device of FIG. 27 during or after a dispensing operation and FIG. 29 shows the device of FIGS. 26-28 during the process of reattaching the protective cap to the housing.

As illustrated in FIG. 27 and as the trigger 180 is depressed the respective motion is transferred via the bridging piece 176 onto the resilient member 173 thus leading to a releasing motion of the catch feature 171 relative to the snap feature 172. As a consequence, the mechanical coupler 160 previously blocked by the interlock 170 is now allowed to move towards the container 132 under the action of the relaxing biasing member 150 as illustrated in FIG. 28. Since the mechanical coupler 160 is connected to and fixed to the moveable part 135 a dispensing operation is conducted and a portion of the fluid is expelled through the outlet 140 and through the orifice 121 as illustrated in FIG. 22.

Now, for biasing the biasing member 150 and for transferring the biasing member 150 into the pre-loaded state as illustrated in FIG. 26 the protective cap 190 has to be reassembled onto the housing 2. As described before the protective cap 190 comprises a cup-shaped hollow interior 191. The protective cap 190 further comprises a longitudinal extension 192. As illustrated in FIG. 23 the extension 192 is provided with a rack portion 168, hence with numerous teeth facing towards the mechanical coupler 160. The mechanical coupler 160 is provided with a corresponding rack portion 163 facing towards the sidewall 124 and hence facing towards the trigger 180. Between the rack portions 163, 168 there is provided a pinion 166 rotatably mounted in the housing 102.

Figure 29:
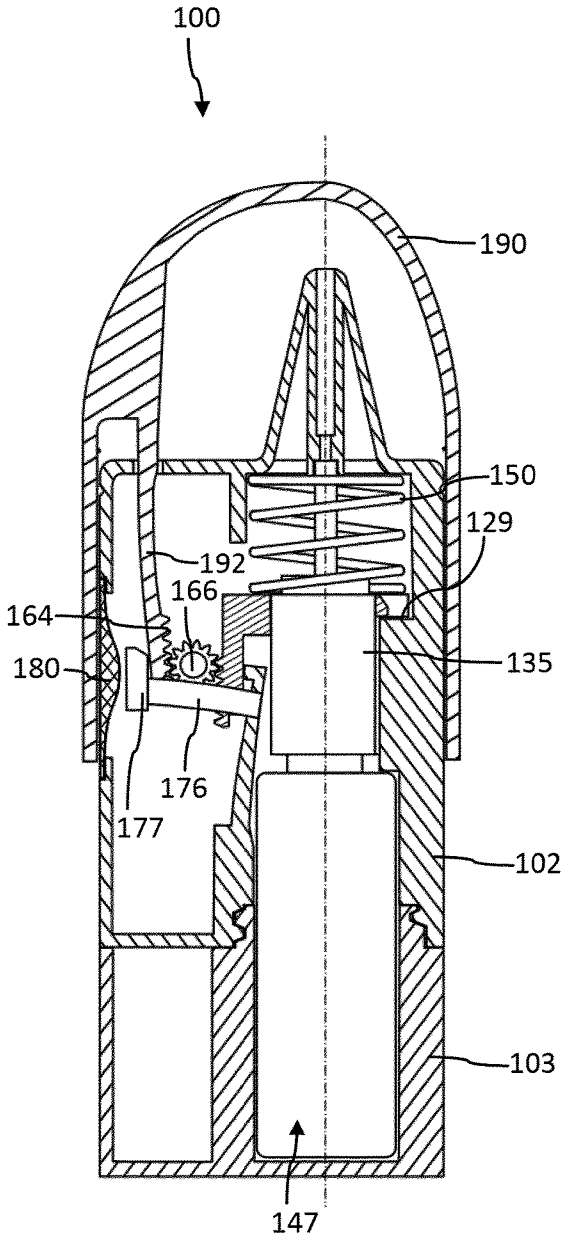

In the configurations as illustrated in FIGS. 28 and 29 the free end of the resilient member 173 has entered a receptacle 167 of the mechanical coupler 160 and is hence hindered to relax back into the initial configuration as illustrated in FIG. 20. Here, the resilient member 173 is in engagement with a sidewall of the receptacle 167. In order to provide a resilient return movement of the resilient member 173 the mechanical coupler 160 has to be displaced back into the preload position as illustrated in FIG. 26. The catching and a longitudinal guiding of the free end of the resilient member 173 and the leg 174 in the receptacle 167 is accompanied by a respective displacement of the bridging piece 176. Hence, even when the trigger 180 has been released, the bridging piece 176 rests in the depressed position because it is fixed to the resilient member 173.

The bridging piece 176 may be further provided with a guiding structure 177 effective to keep the rack portion 168 of the longitudinal extension 192 in engagement with the pinion 66. The further rack portion 163 of the mechanical coupler 160 is permanently engaged with the pinion 166. As the protective cap 190 is now pushed into the closing position when starting from the configuration as illustrated in FIG. 29 the rack portion 168 of the longitudinal extension 192 is kept in engagement with the pinion 166. As the protective cap 190 is moved closer to the closing position as illustrated in FIG. 26 the pinion 166 starts to rotate, thus transferring a respective counter-directed motion onto the rack portion 163. As the protective cap 190 is moved closer to the bottom of the housing 102 the mechanical coupler 60 is moved further away from the bottom and towards the upper end face 123.

This movement continues until the interlock 170 is activated again and until the catch feature 171 of the resilient member 173 is aligned with a recessed portion of the snap feature 172. As the catch feature 171 and the snap feature 172 are properly aligned, the resilient member 173 is allowed to bend outwardly, thus leading to an engagement of the catch feature 171 with the snap feature 172. Then, the interlock 170 is activated, hence interlocked. The mechanical coupler 160 is hindered to move under the action of the biasing member 150. The biasing member 150 is retained in the pre-loaded state as illustrated in FIGS. 26 and 27. Moreover, the lateral or relaxing movement of the resilient member 173 has the further effect that the bridging piece 176 gets in abutment with an inside of the trigger 180 as illustrated in FIG. 26. The longitudinal extension 192 that was bent towards the pinion 176 by the guiding structure 177 of the bridging piece 176 also relaxes into an initial state according to which the rack portion 168 of the longitudinal extension 192 disengages from the pinion 166.

Also here and as it is apparent from FIG. 26, the sidewall 194 of the protection cap 190 completely covers the trigger 180 and thus impedes and effectively blocks any actuation of the trigger 180 as long as the protective cap 190 is in the closing position.

In the example as illustrated in FIGS. 26-32 a further safety arrangement 110 has been implemented with the fluid dispensing device 100. Also here the housing 102 comprises a closure 103 forming a bottom 104 of the housing 102. As it is apparent from FIGS. 30 and 31 the closure 103 comprises a threaded portion 107 complementary-shaped to a threaded portion 106 of the housing 102. The threaded portions 106, 107 are effective to form a threaded connection 105 between the housing 102 and the closure 103. By way of the threaded connection 5, which may also be implemented as a bayonet connection, the closure 103 can be detached from the housing 102. As illustrated in FIGS. 27-32 the closure 3 comprises a cup-shaped compartment 147 configured to receive the container 132 of the spray delivery device 130.

Figure 30:
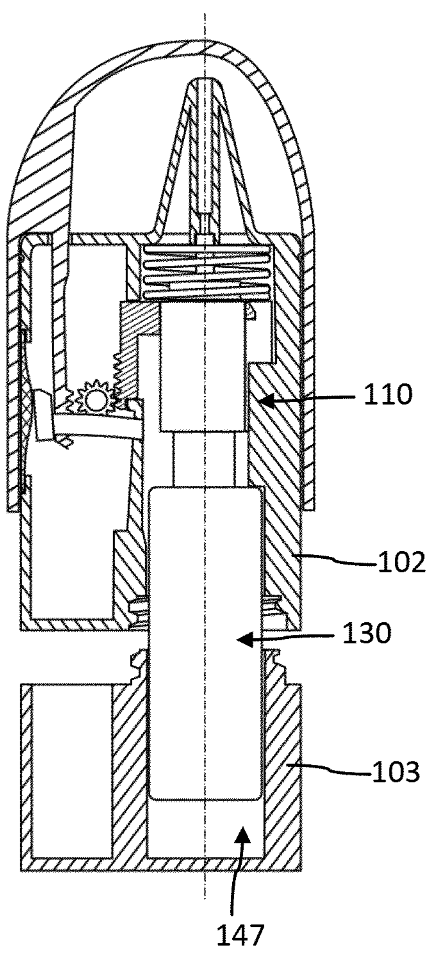
FIG. 30 shows the device of FIGS. 27-29 with the closure detached from the housing.
Figure 31:
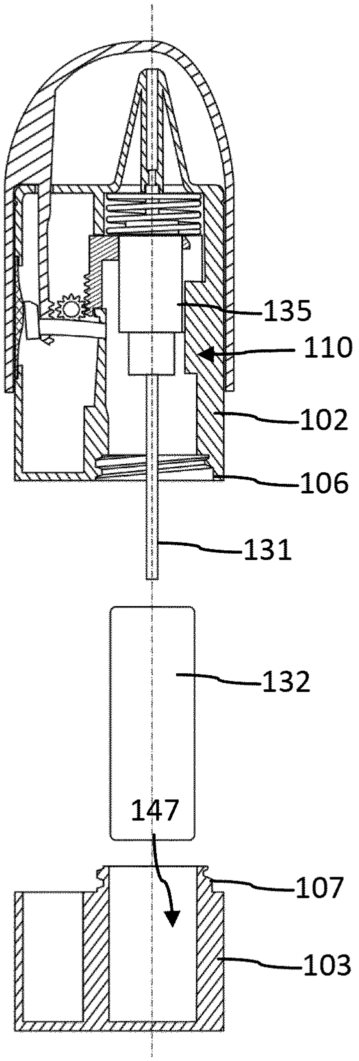
FIG. 31 shows the device of FIG. 30 during replacement of a container of the spray delivery device.

By transferring the closure from the closed position as shown in FIGS. 27-29 into the open position as illustrated in FIGS. 30 and 31, access is provided at least to the container 132 of the spray delivery device 130. Accordingly, and when the closure 103 is disconnected from the housing 102 the user may easily grip the container 132 and may replace the container 132. As shown in FIG. 31 the spray delivery device 130 comprises an elongated tube 131 extending from the moveable part 135 of the spray delivery device into the interior of the container 132. In the illustrated example the container 132 may be detachably or releasably connected to the moveable part 135. The container 132 may be provided with a pierceable seal at an upper end, which seal is penetrated by the tube 131 when the container 132 is connected to the moveable part 135.

As described above the moveable part 135 is connected to and is mechanically engaged with the mechanical coupler 160 that provides a carrier 164 for the spray delivery device 130. The carrier 164 and hence the mechanical coupler 160 is moveable only with regard to a limited longitudinal distance relative to the housing 102. In the unbiased position, as illustrated in FIG. 29, the carrier 164 is in abutment with an abutment face 129, e.g. protruding inwardly from a sidewall of the housing 102. When in abutment with the abutment face 129 through the action of the biasing member 150 the carrier 164 cannot be moved any further by the biasing member 150. When the closure 103 is detached from the housing 102 starting from a configuration as illustrated in FIG. 29 the container 132 is out of or is located remote from a flux of force of the mechanical biasing member 150.

Moreover, since the container 132 as illustrated in the example of FIGS. 26-32 is not subject to a movement relative to the housing 102 it can be generally arranged outside the flux of force provided by the mechanical biasing member 150 for initiating a spray discharge of the spray delivery device 130. For instance, a base 145 of the spray delivery device 130 may be fixed to the housing 102 such that generation of a spray delivery under the action of the relaxing mechanical biasing member 150 only induces a relative motion of the moveable part 135 relative to the base 145 of the spray delivery device 130.

When the base 145 is fixed to the housing 102 the container 132 can be exchanged rather easily and without a danger that the mechanical biasing member 150 becomes subject to a self-actuated disassembly when the closure 103 is detached from the housing 102.

Figure 32:
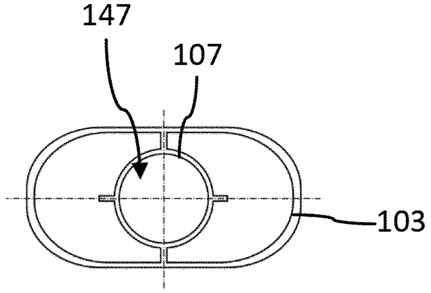
FIG. 32 is illustrative of a top view of one example of the closure.

The cross-sections according to FIGS. 26-31 illustrate a longitudinal cross-section A-A along an L-shaped cross section through an oval-shaped housing 102 in accordance to the schematic sketch at the bottom of FIG. 26. From the top view of the closure 103 as illustrated in FIG. 32 it is immediately apparent, that the threaded portion 107 is located in a center of the closure 103 and that the closure 103 is symmetric along the two main axes of its oval shape.

The safety arrangement 110 as illustrated in FIGS. 26-32 is implemented by arranging and fixing the base 145 to the housing 102 and by providing a mechanical biasing member 150 between the housing 102 and the movable part 135 of the spray delivery device 130. In this way the replaceable container 132 is located outside a flux of force emanating from the biasing member 150. Opening of the closure 103 can be provided either with the mechanical biasing member in the preloaded state or in the unloaded state. When the closure 103 is transferred into the opened position there is no need to block or to prevent a release of mechanical energy of the mechanical biasing member 150.

Figure 33:
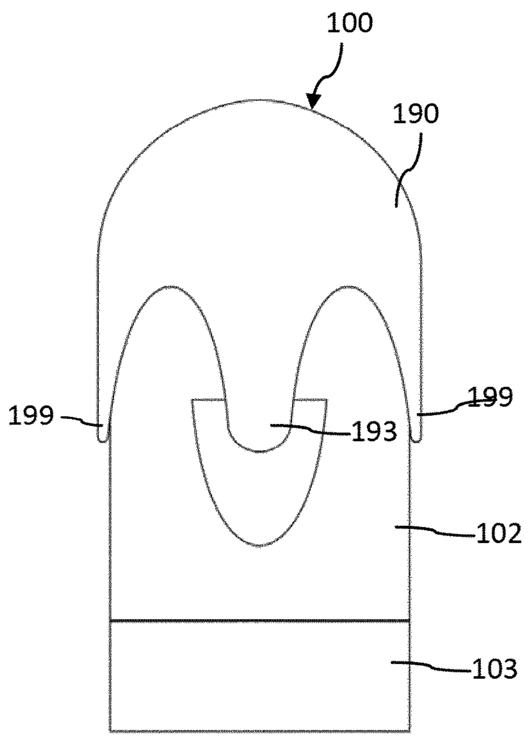
FIG. 33 shows a side view of another example of a fluid dispensing device.

In FIGS. 33-45 a further example of a fluid dispensing device 100 is illustrated. In FIG. 33 the fluid dispensing device is shown from the side and in FIG. 34 it is shown in an orientation rotated by 90° with regard to its longitudinal axis. FIG. 33 represents a front view, wherein the protective cap 190 is pivotally attached to the housing 102.

Figure 36:
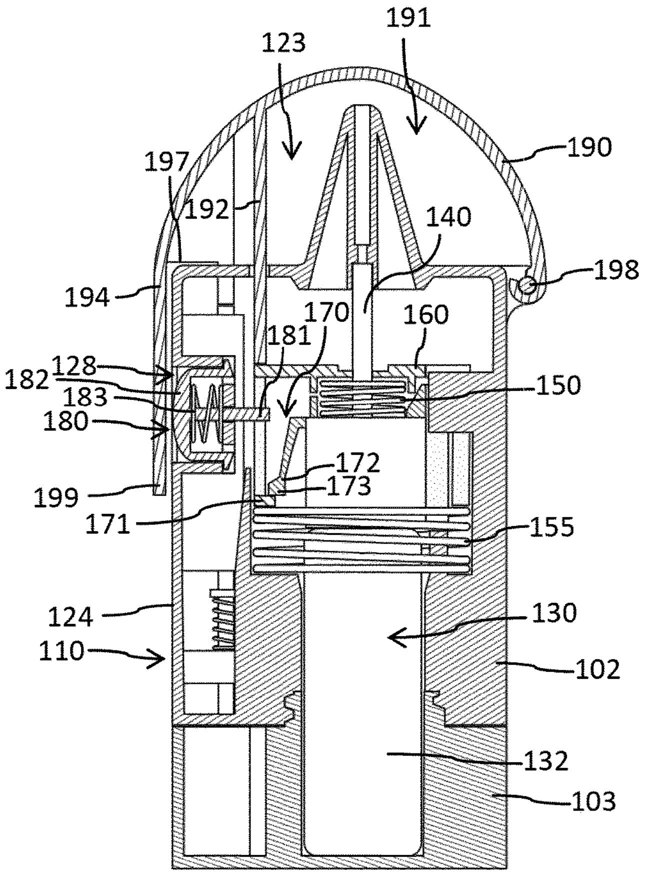
FIG. 36 shows a cross-section through the device of FIGS. 33-35.

The cross-section of FIG. 36 represents a cross-section B-B along the L-shaped line as illustrated in the bottom of FIG. 36. The protective cap 190 is pivotally attached to the housing 102 and is pivotable with regard to a pivot axis 198. The protective cap 190 comprises a hollow interior 191. From the top of the cap and inwardly inside the protective cap 190 there extends an elongated protrusion 192. As described before, the elongated protrusion 192 is configured and operable to enter and to penetrate a slit-shaped through opening 122 provided in an upper end face 123 of the housing 102.

The protective cap 190 may be further provided with a handle section 193 located between extensions 199 of the sidewall 194 of the protective cap 190. In the closing position as illustrated in FIG. 30 the extensions 199 effectively cover at least one trigger 180. The trigger 180 comprises an elongated pin 181 extending into the interior of the housing 102. The trigger 180 further comprises a button 182 spring biased by a spring 183 in a receptacle 128 provided in the sidewall 124 of the housing 102.

Figure 34:
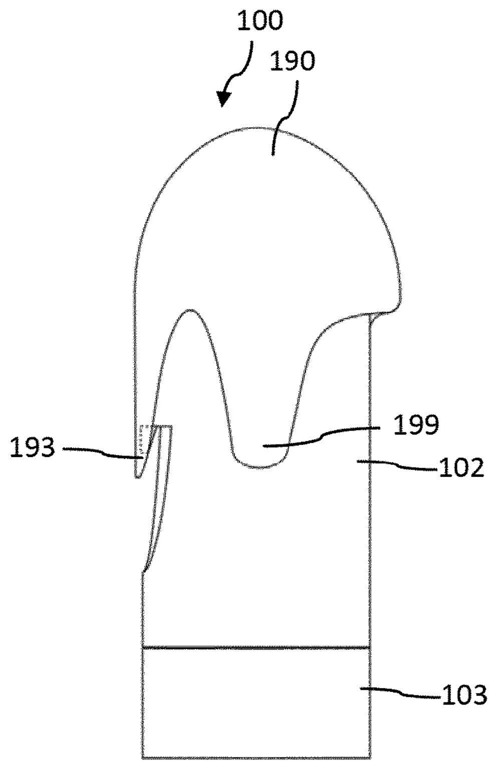
FIG. 34 shows another side view of the fluid dispensing device of FIG. 33 rotated by 90° with the longitudinal axis as an axis of rotation.
Figure 35:
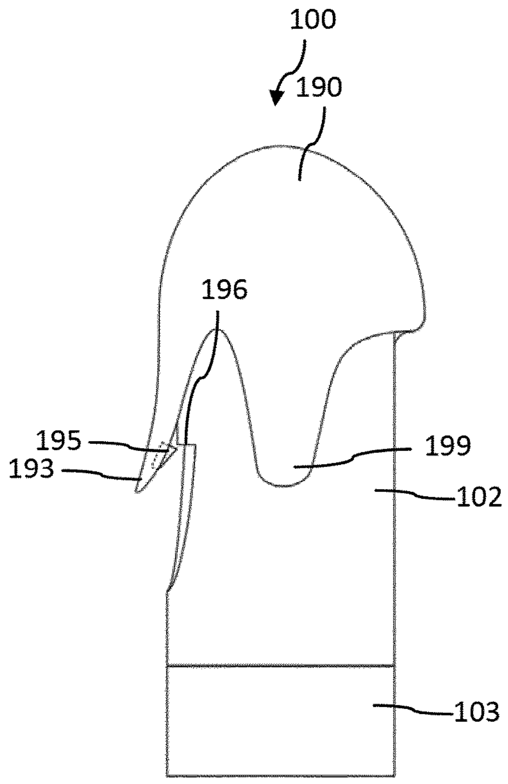
FIG. 35 shows a configuration of the device of FIG. 34 during release of the protective cap.

In the closing position, the handle 193 may snap fit with the housing 102 as indicated in FIG. 34. Here, an inside of the protective cap 190 is provided with a fastening feature 195 configured to engage with a corresponding counter-fastening feature 196 provided on the outside of the housing 102.

In addition and in order to limit a closing movement of the protective cap 190, there is provided an inwardly extending protruding abutment 197 that is configured to engage with the end face 123 of the housing 102, in particular with a corner section of the end face 123.

Figure 37:
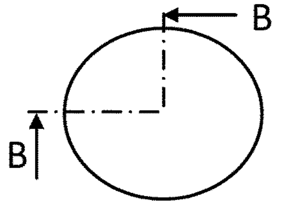
FIG. 37 shows the device of FIG. 36 with the protective cap in the open position.
Figure 37:
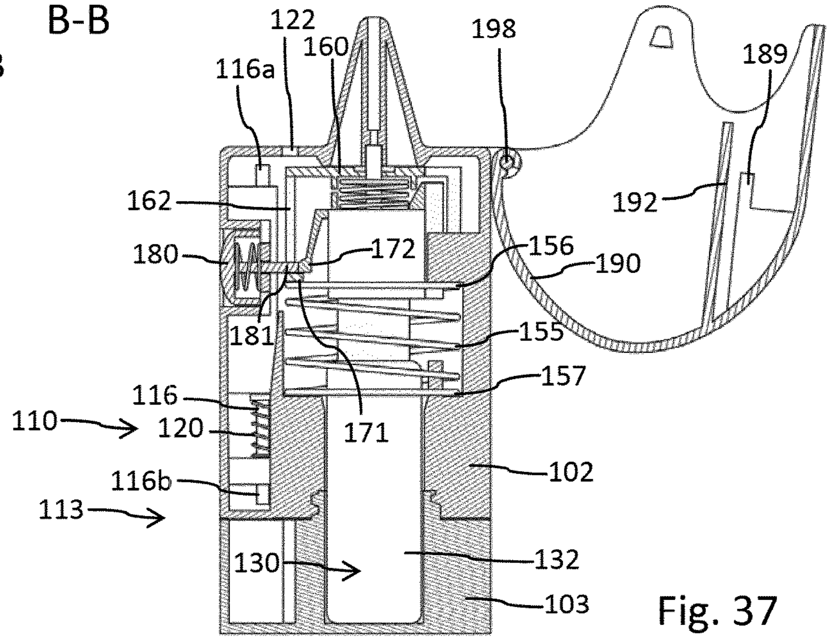
Figure 38:
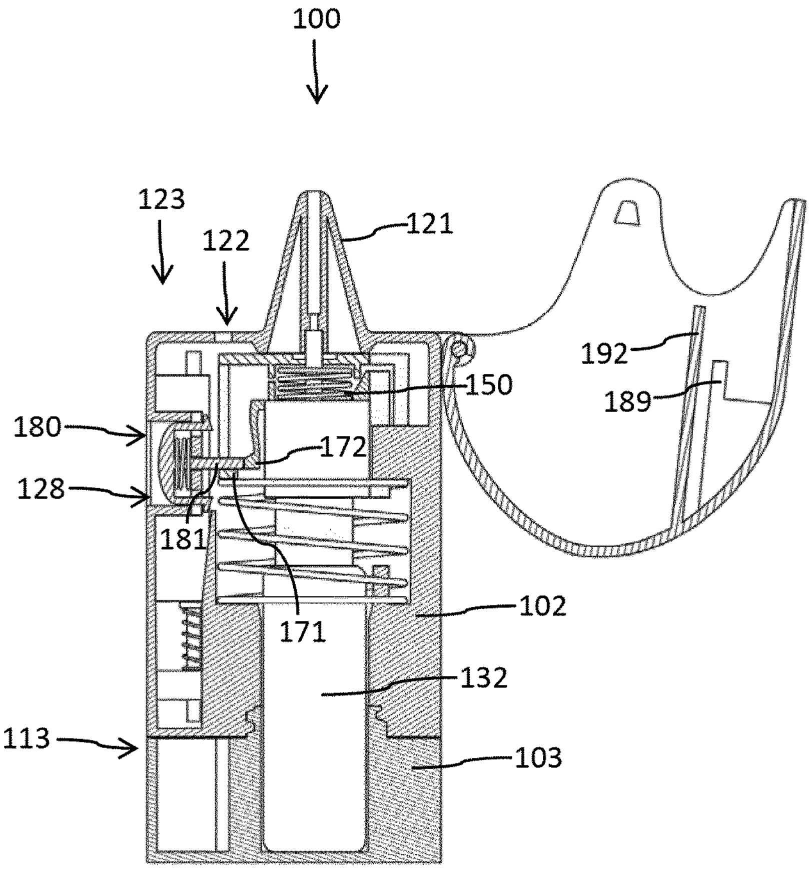
FIG. 38 shows the device of FIG. 37 after or during actuation of the trigger.

In the present example the biasing member 150 is located between the mechanical coupler 160 and the moveable part 135 of the spray delivery device 130. The container 132 of the spray delivery device 130 is fixedly attached inside the housing 102. There is further provided an auxiliary spring 155 that is in engagement with the housing 102 and the mechanical coupler 160. A first end 156 of the auxiliary spring 155 is in abutment with an extension 162 of the mechanical coupler 160 as best illustrated in FIG. 37. At an end facing away from the rather planar-shaped or disc-shaped mechanical coupler 160 of the extension 162 there is provided and arranged the catch feature 171 of the interlock 170. The complementary-shaped snap feature 172 is provided at a free end of a resilient member 173 connected to or integrally formed with the moveable part 135 of the spray delivery device 130.

Similar to examples as described above the longitudinal extension 192 is effective to apply a displacement force onto an abutment 161 of the mechanical coupler 160 so as to activate the interlock 170. Here, the interlock 170 is formed between the mechanical coupler 160 and the moveable part 135 of the spray delivery device 130. As illustrated in FIG. 36, there is a mutual engagement or abutment between the catch feature 171 of the mechanical coupler 160 and the snap feature 172 of the moveable part 135 of the spray delivery device 130.

The mutually corresponding fastening and counter-fastening features 195, 196 keep the protective cap 190 in the closing position and serve to retain the auxiliary spring 155 in the biased state as illustrated in FIG. 30. As the protective cap 190 is pivoted into the opening position as illustrated in FIGS. 31 and 32 there is no further downwardly acting force present on the mechanical coupler 160. Insofar, the auxiliary spring 155 is operable to displace the assembly of the mechanical coupler 160 and the moveable part 135 away from the container 132. The biasing member 150 is kept in the pre-loaded state during this translational movement because both, the moveable part 135 and the mechanical coupler 160 are subject to a common displacement relative to the housing 102 as induced by the auxiliary spring 155.

Figure 39:
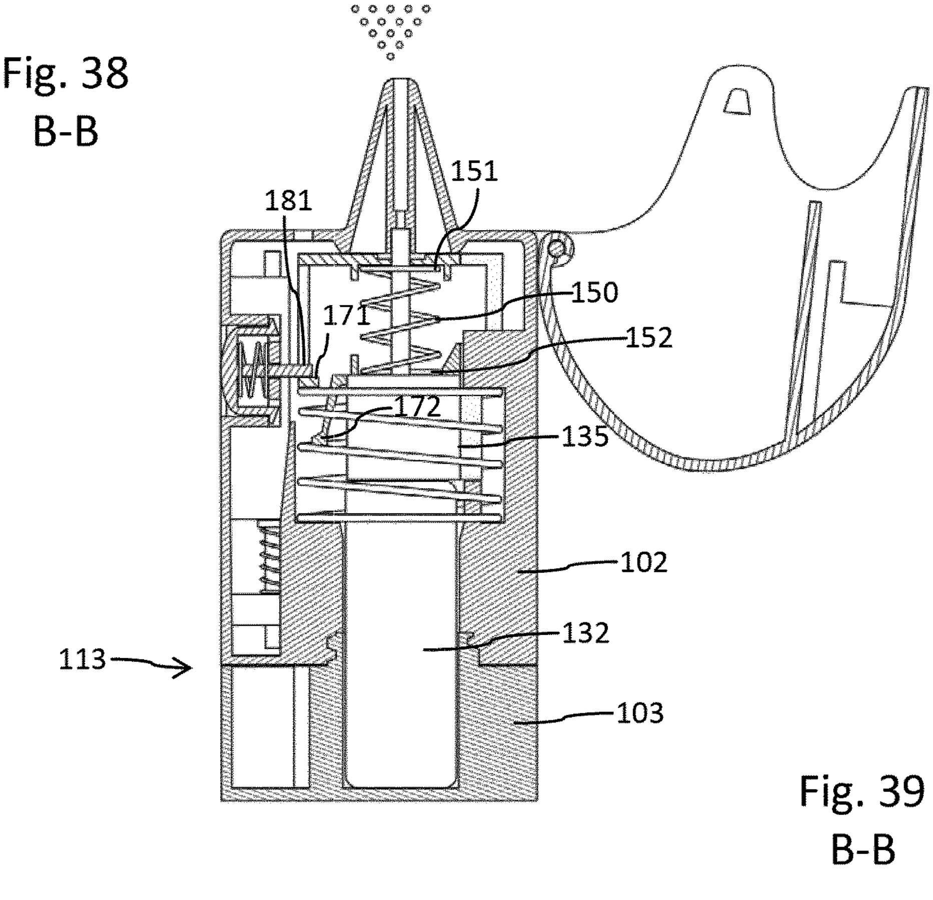
FIG. 39 shows the device of FIG. 38 during or after dispensing of a dose of the fluid.

This movement as induced by the auxiliary spring 155 brings the snap feature 172 in alignment with the pin 181 of the trigger 180. As the trigger 180 is then depressed the snap feature 172 disengages from the catch feature 171. The mechanical coupler 160 is kept in engagement with the upper end or with the end face 123 of the housing 102 by the auxiliary spring 155. Upon release of the interlock 170 the moveable part 135 will then become subject to a movement relative to the housing 102 and relative to the mechanical coupler 160 because of the relaxing motion of the biasing member 150. Consequently, the moveable part 135 is moved towards the container 132 and a predefined amount of the fluid or medicament will be expelled through the orifice 121 as illustrated in FIG. 39.

As the lid or protective cap 190 is closed again the longitudinal extension 192 enters the slit-shaped through opening 122 in the end face 123 of the housing 102. There, the longitudinal extension 192 gets in engagement with the abutment section 161 of the mechanical coupler 160. Consequently, the mechanical coupler 160 is displaced towards the container 130 until the interlock 170 is engaged again and until the auxiliary spring 155 reaches a pre-loaded state as illustrated in FIG. 36.

The mechanical coupler 160 and the moveable part 135 each comprise two diametrically opposed mutually corresponding snap features 172 and catch features 171, respectively. Moreover, the fluid dispensing device 100 may comprise two triggers 180. In this way, any forces for pre-loading of the biasing member 150, the auxiliary spring 155 as well as any forces for disengaging the interlock 170 can be symmetrically distributed and introduced into the respective components of the fluid dispensing device 100. Also the protective cap 190 may comprises two longitudinal extensions 192 in order to apply a biasing force onto the mechanical coupler 160 rather symmetrically.

Also here and as long as the protective cap 190 is in the closing position actuation of the trigger 180 is effectively blocked.

Figure 40:
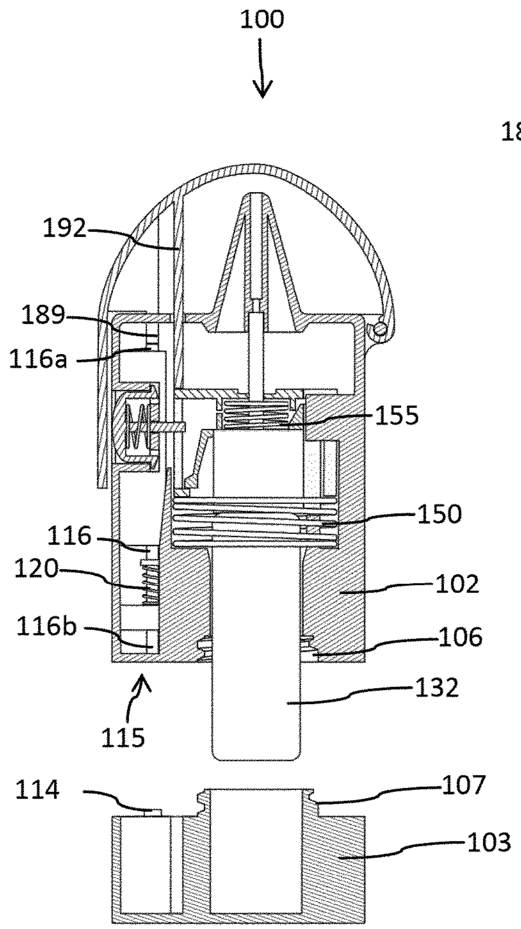
FIG. 40 shows the device of FIGS. 33-39 with the closure detached from the housing.
Figure 41:
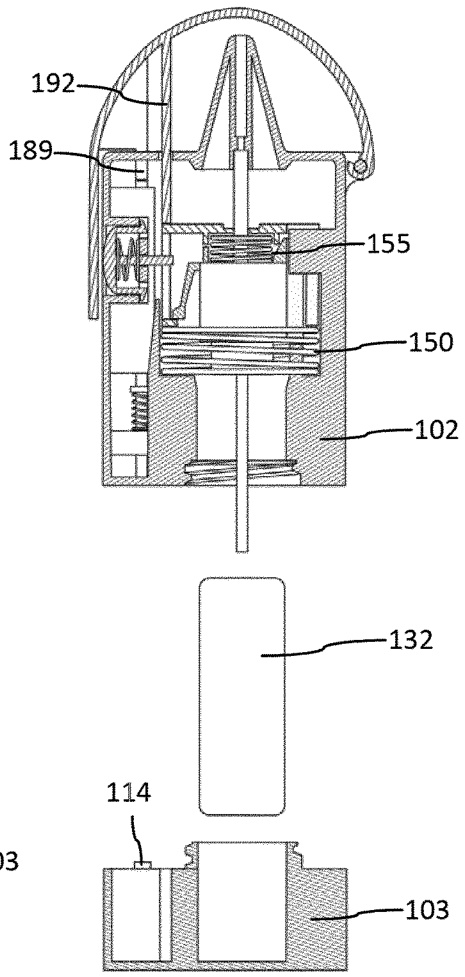
FIG. 41 shows the device of FIG. 40 during replacement of a container of the spray delivery device.
Figure 42:
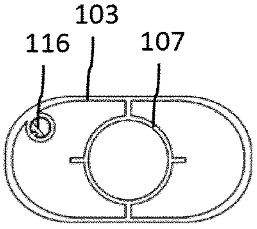
FIG. 42 is illustrative of a top view of an example of the closure.

In the examples of FIGS. 33-45 the safety arrangement 110 comprises a closure lock 113. The closure lock 113 is operable to prevent transferring of the closure 103 from the closed position as illustrated in FIGS. 36-39 into the open position as illustrated in FIGS. 40 and 41. The closure lock 113 comprises a latch 114 provided on the closure 103. The closure lock 113 further comprises a latch keeper 115 on or in the housing 102. When the closure 103 is in the closed position the latch 114 is engaged with the latch keeper 115.

Figure 43:
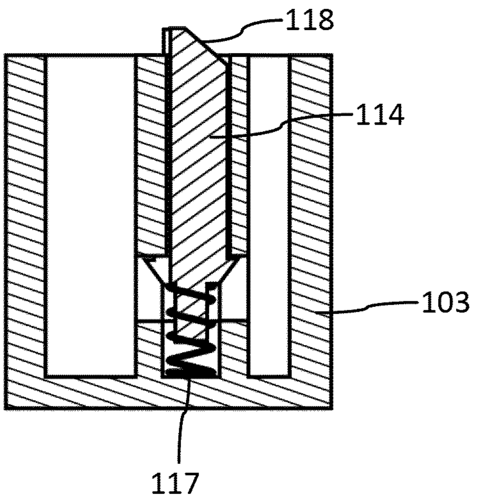
FIG. 43 shows an example of a closure lock in a locked state.
Figure 44:
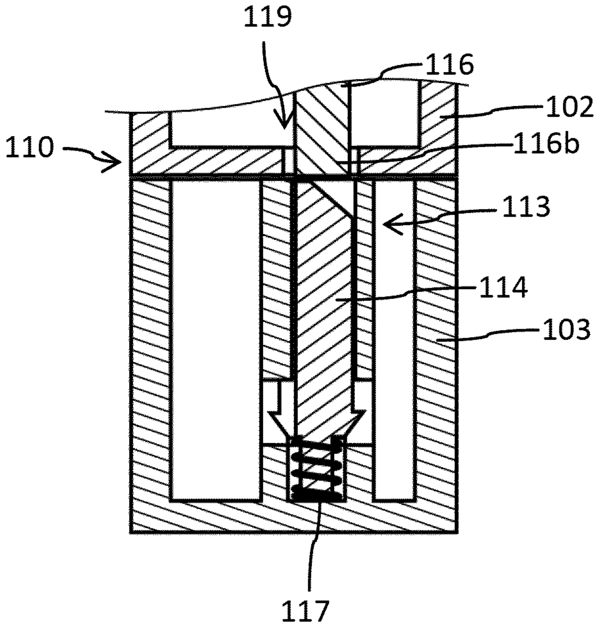
FIG. 44 shows the closure lock of the closure in an unlocked state and FIG. 45 shows the closure lock in the locked state when the closure is locked to the housing of the fluid dispensing device.
Figure 45:
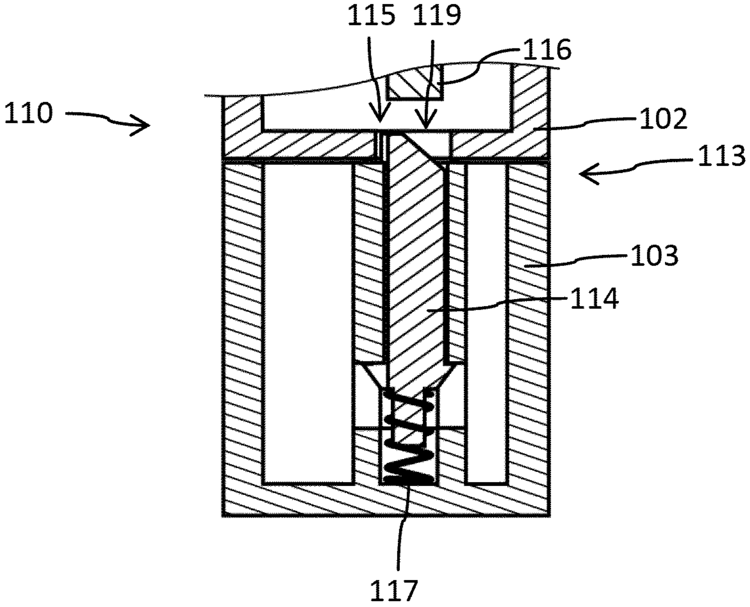

In the detailed illustration of FIGS. 43-45 the closure 103 comprises a latch 114 slidably disposed in or on the closure 103. The latch 114 is displaceable against the action of a restoring element 117, e.g. implemented as a return spring. Here, the restoring element 117 serves to urge the latch 114 into a latching position, in which at least a portion, e.g. an upper end of the latch 114 protrudes from an upper end of the closure 103. The latch 114 is provided with a beveled edge 118 at its free end, hence at a protruding portion.

The closure 103 is connectable to the housing 102 by a threaded joint or by a bayonet joint through interaction of the threaded portion 107 of the closure 103 engaging with a correspondingly shaped threaded portion 106 of the housing 102. As the closure 103 is assembled and fixed to the housing 102 the beveled edge 118 may serve to urge the latch 114 into a retracted position as indicated in FIG. 44.

When reaching a final assembly configuration as illustrated in FIG. 44, in which the closure 103 has reached the closed position, the latch 114 longitudinally aligns with a through opening 119 or with a recess provided in a portion of the housing 102 adjacent to the upper side of the closure 103. As illustrated in FIG. 45 and under the effect of the restoring element 117 the latch 114 is urged upwardly and enters the through opening 119. In this configuration a mutual rotation of the closure 103 relative to the housing 102 is effectively blocked.

For transferring the closure lock 113 into an unlocked state as illustrated in FIG. 44 a closure lock rod 116 is urged downwardly and engages the free end of the latch 114. The closure lock rod 116 comprises a second end 116*b* configured to displace the latch 114 into the configuration as illustrated in FIG. 44, in which the latch 114 is retracted in the closure 103 and in which the latch 114 does no longer protrude from the closure 103.

The closure lock rod 160 is engaged with another restoring element 120, e.g. implemented as a compression spring. The restoring element 120 serves to displace the closure lock rod 116 away from the closure 103 so that the latch 114 protrudes from the closure 103. The closure lock rod 116 extends through the housing 102. The closure lock rod 116 comprises a first end 116*a* located at or near the upper end of the housing 102. The first end 116*a* is configured to mate or to engage with a correspondingly shaped pin 189 of the protective cap 190.

As the protective cap 190 is transferred from an open position as illustrated in FIG. 37 into a closing position as shown in FIG. 40 the pin 189 engages with the first end 116*a* of the closure lock rod 116 and urges the closure lock rod 116 downwardly against the action of the restoring element 120. When the closure 103 is appropriately connected to the housing 102 and when the latch 114 is appropriately aligned with the latch keeper 115 the closure lock rod 116 is pushed downwardly, e.g. towards the closure 103, thereby urging the latch 114 out of engagement from the latch keeper 115.

In this way the safety arrangement 110 is operable to prevent a movement of the closure 103 from the closed position towards the open position as long as the mechanical biasing member 150 is in the pre-loaded state or as long as the mechanical biasing member 150 is transferrable from the pre-loaded state into the unloaded state. Moreover, the safety arrangement 110 is configured to prevent transferring of the closure 103 from the closed position towards and into the open position as long as the protective cap 190 is in the open position and as long as the protective cap 190 has not reached the closing position.

With other examples (not illustrated) the closure lock rod 116 is operably engaged with one of the interlock 170 and the trigger 180. The closure lock rod 116 reaches a release or unlocked configuration as illustrated in FIG. 44 only when the mechanical energy of the mechanical biasing member has been released, e.g. by actuation of the trigger 180 and/or by transferring of the interlock 170 into the unlocked state. In this way, the safety arrangement 110 is configured to prevent a movement of the closure 103 towards the open position as long as the mechanical biasing member 150 is in the preloaded state.

Figure 46:
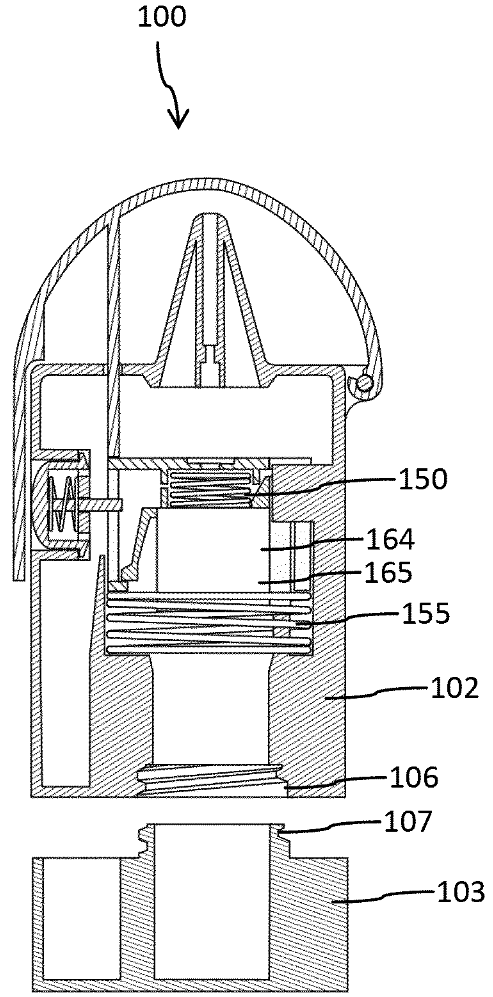
FIG. 46 shows another example of the fluid dispensing device.
Figure 47:
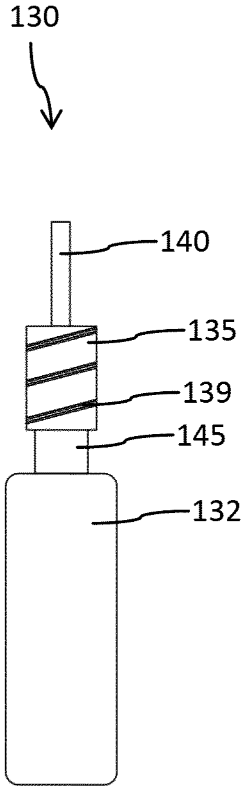
FIG. 47 is illustrative of a further example of the spray delivery device.

With the further example as illustrated in FIGS. 46 and 47 the movable part 135 of the spray delivery device 130 comprises a threaded portion 139 on or at the movable part 135. Here, the entire spray delivery device 130 may be detachably mounted and fixed to a correspondingly shaped threaded portion of the housing 102 by the threaded portion 139. The fluid dispensing device 100 comprises a carrier 164 comprising a carrier sleeve 165 with an inner thread mating with the outer threaded portion 139 of the movable part 135.

The container 132 and optionally also a base 145 is or are rotationally locked to the movable part 135. As the closure 103 is detached from the housing 102 a lower end of the container 132 protrudes from a lower end of the housing 102 and is easily grippable by a user. The user may apply a torque and may unscrew the threaded connection between the movable part 135 and the carrier 164. In this way, the entire spray delivery device 130 can be replaced by another spray delivery device 130.

| Reference numbers | |
|---|---|
| 1 | fluid dispensing device |
| 2 | housing |
| 3 | closure |
| 4 | bottom |
| 5 | connection |
| 6 | threaded portion |
| 7 | threaded portion |
| 8 | slit |
| 9 | hinge |
| 10 | safety arrangement |
| 13 | closure lock |
| 14 | latch |
| 15 | latch keeper |
| 18 | recess |
| 20 | housing |
| 21 | orifice |
| 22 | through opening |
| 23 | end face |
| 24 | sidewall |
| 25 | guiding structure |
| 26 | accommodating space |
| 27 | jet nozzle |
| 28 | shaft portion |
| 29 | aperture |
| 30 | spray delivery device |
| 31 | tube |
| 32 | container |
| 33 | inlet valve |
| 35 | moveable part |
| 36 | outlet valve |
| 38 | chamber |
| 39 | shoulder portion |
| 40 | outlet |
| 41 | shaft |
| 42 | spring |
| 45 | base |
| 46 | through opening |
| 47 | compartment |
| 48 | pressure piece |
| 49 | partition wall |
| 50 | biasing member |
| 51 | first end |
| 52 | second end |
| 60 | mechanical coupler |
| 61 | abutment |
| 62 | strut |
| 63 | corner section |
| 64 | carrier |

-continued

| Reference numbers | |
|---|---|
| 65 | sleeve |
| 66 | button |
| 70 | interlock |
| 71 | catch feature |
| 72 | snap feature |
| 73 | resilient member |
| 74 | spring |
| 75 | aperture |
| 80 | trigger |
| 81 | pin |
| 87 | extension |
| 90 | protective cap |
| 90a | cap portion |
| 91 | hollow interior |
| 92 | extension |
| 94 | sidewall |
| 95 | fastening feature |
| 96 | counter-fastening feature |
| 100 | fluid dispensing device |
| 102 | housing |
| 103 | closure |
| 104 | bottom |
| 105 | connection |
| 106 | threaded portion |
| 107 | threaded portion |
| 110 | safety arrangement |
| 113 | closure lock |
| 114 | latch |
| 115 | latch keeper |
| 116 | closure lock rod |
| 116a | first end |
| 116b | second end |
| 117 | restoring element |
| 118 | beveled edge |
| 119 | through opening |
| 120 | restoring element |
| 121 | orifice |
| 122 | through opening |
| 123 | end face |
| 124 | sidewall |
| 125 | guiding structure |
| 126 | accommodating space |
| 128 | receptacle |
| 129 | abutment face |
| 130 | spray delivery device |
| 131 | tube |
| 132 | container |
| 133 | inlet valve |
| 135 | moveable part |
| 136 | outlet valve |
| 138 | chamber |
| 139 | threaded portion |
| 140 | outlet |
| 141 | shaft |
| 142 | spring |
| 145 | base |
| 147 | compartment |
| 150 | biasing member |
| 151 | first end |
| 152 | second end |
| 155 | auxiliary spring |
| 156 | first end |
| 157 | second end |
| 160 | mechanical coupler |
| 161 | abutment |
| 162 | extension |
| 162 | rack portion |
| 164 | carrier |
| 165 | sleeve |
| 166 | pinion |
| 167 | receptacle |
| 168 | rack portion |
| 170 | interlock |
| 171 | catch feature |
| 172 | snap feature |
| 173 | resilient member |
| 174 | leg |

-continued

| Reference numbers | |
|---|---|
| 176 | bridging piece |
| 177 | guiding structure |
| 180 | trigger |
| 181 | pin |
| 182 | button |
| 183 | spring |
| 189 | pin |
| 190 | protective cap |
| 190a | cap portion |
| 191 | hollow interior |
| 192 | extension |
| 193 | handle |
| 194 | sidewall |
| 195 | fastening feature |
| 196 | fastening feature |
| 197 | abutment |
| 198 | pivot axis |
| 199 | extension |

The invention claimed is:

1. A fluid dispensing device comprising:

a housing comprising an orifice, wherein the housing is configured to accommodate at least a portion of a spray delivery device comprising a container and an outlet through which the fluid stored in the spray delivery device can be discharged;

a mechanical biasing member reversibly transferable between a pre-loaded state and an unloaded state and configured to store mechanical energy in the pre-loaded state, effective to produce a spray discharge of the spray delivery device;

a closure fixable to the housing and movable relative to the housing between a closed position and an open position, wherein when in the open position, the container of the spray delivery device is accessible from outside the housing;

a safety arrangement configured to:

prevent a movement of the closure from the closed position towards the open position as long as the mechanical biasing member is in the pre-loaded state, prevent a release of mechanical energy of the pre-loaded mechanical biasing member as long as the closure is not in the closed position, or release a portion of the mechanical energy of the pre-loaded mechanical biasing member during and through a movement of the closure from the closed position towards the open position.

2. The fluid dispensing device of claim 1, wherein the safety arrangement comprises a carrier mechanically engageable with the spray delivery device or with a movable part of the spray delivery device, the carrier being engaged with the mechanical biasing member and being movably disposed inside the housing from an unbiased position against a force effect of the mechanical biasing member towards and into a biased position.

3. The fluid dispensing device of claim 2, wherein when in the biased position the carrier is engaged with the closure and prevents a movement of the closure from the closed position towards the open position.

4. The fluid dispensing device of claim 1, further comprising an interlock configured to be releasable and to retain the mechanical biasing member in the pre-loaded state and further comprising a trigger that is manually actuatable and operationally engaged with the interlock and configured to release the interlock when actuated.

5. The fluid dispensing device of claim 4, wherein the closure is engaged with at least one of the interlock and the trigger and wherein the closure is transferrable or movable from the closed position into the open position only when the interlock is released or when the trigger is actuated.

6. The fluid dispensing device of claim 4, wherein at least one of the trigger and the interlock is operably engaged with the closure and is transferrable into an unlocked state or actuated state only when the closure is in the closed position.

7. The fluid dispensing device of claim 4, wherein a closure lock is operably engaged with at least one of the interlock, the trigger and a protective cap and wherein the closure lock is transferable from the locked state towards or into the unlocked state by the at least one of the interlock, the trigger and the protective cap configured to accommodate the outlet of the spray delivery device.

8. The fluid dispensing device of claim 7, further comprising a closure lock rod slidably disposed in the housing, wherein the closure lock rod comprises a first end and a second end, wherein the first end is configured to engage with one of the interlock, the trigger and the protective cap and wherein the second end is configured engage with the closure lock.

9. The fluid dispensing device of claim 1, further comprising a protective cap configured to accommodate the outlet of the spray delivery device, wherein the protective cap is configured for fitting to the housing at least in a closing position relative to the housing, in which the protective cap covers the orifice.

10. The fluid dispensing device of claim 1, further comprising a closure lock engaged with the housing and the closure, wherein the closure lock is transferrable between a locked state, in which the closure is locked to the housing and an unlocked state, in which the closure is movable relative to the housing.

11. The fluid dispensing device of claim 10, wherein the closure lock comprises a latch on one of the housing and the closure and a latch keeper on the other one of the housing and the closure, wherein the closure lock is in the locked state when the latch is engaged with the latch keeper and wherein the closure lock is in the unlocked state when the latch and the latch keeper are disengaged.

12. The fluid dispensing device of claim 1, wherein the mechanical biasing member comprises a first end and a second end and wherein the first end is operably engaged with the spray delivery device and wherein the second end is engaged with the closure.

13. The fluid dispensing device of claim 1, wherein transferring of the mechanical biasing member between the pre-loaded state and the unloaded state includes a movement of at least a portion of the mechanical biasing member along a longitudinal direction.

14. The fluid dispensing device of claim 13, wherein at least one of the closure and the container is movable along a replacement direction for replacement of the container.

15. The fluid dispensing device of claim 14, wherein the replacement direction extends transverse to the longitudinal direction.

16. The fluid dispensing device of claim 1, wherein the spray delivery device or a portion thereof is arranged inside the housing.

17. The fluid dispensing device of claim 1, wherein the outlet of the spray delivery device coincides with the orifice.

18. The fluid dispensing device of claim 1, wherein the outlet of the spray delivery device is arranged in an alignment with the orifice.

19. The fluid dispensing device of claim 1, wherein the spray delivery device comprises a base, wherein the outlet is movable relative to the base for discharging a dose of the fluid through the outlet.

20. A method for dispensing fluid using a fluid dispensing device comprising:

a housing, the housing comprising an orifice and wherein the housing is configured to accommodate at least a portion of a spray delivery device comprising a container and an outlet through which the fluid stored in the spray delivery device can be discharged, a mechanical biasing member reversibly transferable between a pre-loaded state and an unloaded state and configured to store mechanical energy in the pre-loaded state, effective to produce a spray discharge of the spray delivery device, a closure fixable to the housing and movable relative to the housing between a closed position and an open position, wherein when in the open position, the container of the spray delivery device is accessible from outside the housing, the method comprising:

preventing a movement of the closure from the closed position towards the open position as long as the mechanical biasing member is in the pre-loaded state, preventing a release of mechanical energy of the pre-loaded mechanical biasing member as long as the closure is not in the closed position, or releasing a portion of the mechanical energy of the pre-loaded mechanical biasing member during and through a movement of the closure from the closed position towards the open position.

* * * * *